United States Patent
Castro Pineiro et al.

(10) Patent No.: US 7,253,205 B2
(45) Date of Patent: Aug. 7, 2007

(54) GEM-DISUBSTITUTED CYCLOHEXANE DERIVATIVES AND THEIR USE AS THERAPEUTIC AGENTS

(75) Inventors: Jose Luis Castro Pineiro, Bishops Stortford (GB); Kevin Dinnell, Much Hadham (GB); Jason Matthew Elliott, Felsted (GB); Gregory John Hollingworth, Brentwood (GB); Duncan Edward Shaw, Bishops Stortford (GB); Christopher John Swain, Duxford (GB)

(73) Assignee: Merck Sharp & Dohme Limited, Hoddesdon, Hertfordshire (GB)

( * ) Notice: Subject to any disclaimer, the term of this patent is extended or adjusted under 35 U.S.C. 154(b) by 470 days.

(21) Appl. No.: 10/481,477

(22) PCT Filed: Jun. 10, 2002

(86) PCT No.: PCT/GB02/02654

§ 371 (c)(1),
(2), (4) Date: Dec. 17, 2003

(87) PCT Pub. No.: WO02/102372

PCT Pub. Date: Dec. 27, 2002

(65) Prior Publication Data

US 2004/0171642 A1     Sep. 2, 2004

(30) Foreign Application Priority Data

Jun. 18, 2001   (GB) ................... 0114867.5

(51) Int. Cl.
*A61K 31/4545*   (2006.01)
*C07D 401/02*   (2006.01)

(52) U.S. Cl. .......... 514/424; 514/217.03; 514/227.8; 514/231.5; 514/252.13; 514/326; 514/422; 540/435; 544/60; 544/141; 544/372; 546/192; 548/518; 548/541

(58) Field of Classification Search ........... 548/543; 514/424, 217.03, 227.8, 231.5, 252.13, 326, 514/422; 540/435; 544/60, 141, 372; 546/192
See application file for complete search history.

(56) References Cited

U.S. PATENT DOCUMENTS 5,776,959 A    7/1998  Ferrendelli et al.

FOREIGN PATENT DOCUMENTS

WO     WO 98 03493     1/1998
WO     WO 01 87866 A   11/2001

OTHER PUBLICATIONS

Koskinen et al., CA 1989:173728.*
Ohba et al., CA 1991:247145.*
Yui et al., CA 2000:583935.*
Exhibit 1—STN search results for starting material.*
Severini et al., The Tachykinin Peptide Family, Pharmacological Reviews 54(2):285-322 (2002).*
Hollingworth, et al, Bioorganic & Medicinal Chemistry Letters, 16 (2006), 1197-1201.
"Label" information for Emend as of Jun. 30, 2006.

* cited by examiner

*Primary Examiner*—Zinna N. Davis
(74) *Attorney, Agent, or Firm*—Curtis C. Panzer

(57) ABSTRACT

The present invention relates compounds of the formula (I): wherein $R^1$, $R^2$, $R^3$, $R^4$, $R^5$, $R^6$, $R^7$, $R^8$, $R^9$ and $R^{10}$ represent a variety of substituents, ring A is a phenyl or pyridyl ring; d is zero, 1 or 2; and pharmaceutically acceptable salts and N-oxides thereof. The compounds are of particular use in the treatment or prevention of depression, anxiety, pain, inflammation, migraine, emesis or postherpetic neuralgia

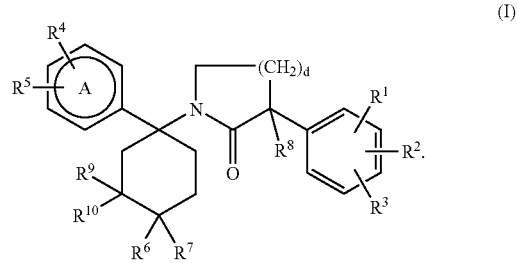

(I)

16 Claims, No Drawings

GEM-DISUBSTITUTED CYCLOHEXANE DERIVATIVES AND THEIR USE AS THERAPEUTIC AGENTS

CROSS REFERENCE TO RELATED APPLICATIONS

This application is a U.S. National Phase application under 35 U.S.C. § 371 of PCT Application No. PCT/GB02/02654, filed Jun. 10, 2002, which claims priority under 35 U.S.C. § 119 from GB Application No. 0114867.5, filed Jun. 18, 2001.

This invention relates to a class of gem-disubstituted cyclohexane derivatives which are useful as tachykinin antagonists. More particularly, the compounds of the invention are useful as neurokinin 1 (NK-1) receptor antagonists.

The present invention provides compounds of the formula (I):

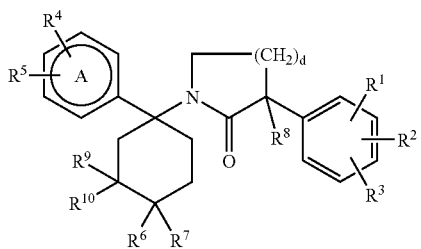

wherein ring A is a phenyl or pyridyl ring;

$R^1$ represents hydroxy, $C_{1-6}$alkyl, fluoro$C_{1-6}$alkyl, $C_{2-6}$alkenyl, $C_{3-7}$cycloalkyl, $C_{3-7}$cycloalkyl$C_{1-6}$alkyl, $C_{1-6}$alkoxy, fluoro$C_{1-6}$alkoxy, $C_{1-6}$alkoxy$C_{1-4}$alkyl, $C_{1-6}$alkoxy$C_{1-4}$alkoxy, fluoro$C_{1-6}$alkoxy$C_{1-4}$alkoxy, $C_{2-6}$alkenyloxy, $C_{3-7}$cycloalkoxy, $C_{3-7}$cycloalkyl$C_{1-4}$alkoxy, phenoxy, cyano, halogen, $NR^aR^b$, $SR^a$, $SOR^a$, $SO_2R^a$, $OSO_2R^a$, $NR^aCOR^c$, $COR^a$, $CO_2R^a$ or $CONR^aR^b$ where $R^a$ and $R^b$ each independently represent hydrogen, $C_{1-4}$alkyl, $C_{3-5}$cycloalkyl, fluoro$C_{1-4}$alkyl or $CH_2CO_2C_{1-4}$alkyl, and $R^c$ represents $C_{1-6}$alkyl, $C_{1-6}$alkoxy, fluoro$C_{1-6}$alkyl or phenyl;

$R^2$ represents hydrogen, halogen, $C_{1-6}$alkyl or $C_{1-6}$alkoxy;

or when $R^2$ is adjacent to $R^1$, they may be joined together such that there is formed a 5- or 6-membered saturated or unsaturated ring containing one or two atoms selected from nitrogen, oxygen and sulphur, which ring is optionally substituted by a group selected from $C_{1-4}$alkyl, $CF_3$, =O or =S;

$R^3$ represents hydrogen, halogen, $C_{1-6}$alkyl, fluoro$C_{1-6}$alkyl, $C_{1-6}$alkoxy, fluoro$C_{1-6}$alkoxy, $C_{3-7}$cycloalkyl, $C_{3-7}$cycloalkyl$C_{1-4}$alkyl, cyano, $SR^a$, $SOR^a$, $SO_2R^a$, $NR^aR^b$, $NR^a$-$COR^c$, $COR^a$, $CO_2R^a$, $CONR^aR^b$ or $C_{1-4}$alkyl substituted by cyano, $CO_2R^a$ or $CONR^aR^b$ where $R^a$, $R^b$ and $R^c$ are as previously defined;

or $R^3$ represents a 5- or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalkyl, $C_{3-7}$cycloalkyl$C_{1-4}$alkyl, trifluoromethyl, $OCF_3$, $NO_2$, $CN$, $SR^a$, $SOR^a$, $SO_2R^a$, $COR^a$, $CO_2R^a$, phenyl, —$(CH_2)_rNR^aR^b$, —$(CH_2)_rNR^aCOR^b$, —$(CH_2)_rCONR^aR^b$, or $CH_2C(O)R^a$, where $R^a$ and $R^b$ are as previously defined and r is zero, 1 or 2;

$R^4$ represents hydrogen, halogen, $C_{1-6}$alkyl, $C_{1-6}$alkoxy, fluoro$C_{1-6}$alkyl, fluoro$C_{1-6}$alkoxy, hydroxy, $NO_2$, $CN$, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

$R^5$ represents hydrogen, halogen, $C_{1-6}$alkyl, fluoro$C_{1-6}$alkyl or $C_{1-6}$alkoxy substituted by $C_{1-4}$alkoxy;

$R^6$ represents hydrogen, hydroxy or a $C_{1-4}$alkyl group optionally substituted by a hydroxy group;

$R^7$ represents hydrogen, hydroxy, —$(CH_2)_nNR^{11}R^{12}$, —$(CH_2)_nCO_2R^a$, carbocyclyl, C-linked heterocyclyl or heteroaryl, where $R^a$ is as previously defined;

or $R^6$ and $R^7$ together represent =O, =CHCO$_2R^a$ or —O(CH$_2)_m$O—, where $R^a$ is as previously defined;

$R^8$ represents hydrogen, hydroxy, $C_{1-6}$alkyl, $C_{1-6}$alkoxy, hydroxy$C_{1-6}$alkyl, $C_{2-6}$alkenyl, $C_{2-6}$alkynyl, $C_{1-4}$alkyl substituted by $C_{1-4}$alkoxy or $C_{1-6}$alkoxy substituted by $C_{1-4}$alkoxy;

$R^9$ represents hydrogen, halogen or hydroxy and $R^{10}$ represents hydrogen;

or $R^9$ and $R^{10}$ both represent fluorine or together represent oxo (=O);

$R^{11}$ and $R^{12}$ each independently represent hydrogen, $C_{1-6}$alkyl, $C_{2-6}$alkenyl, hydroxy$C_{1-6}$alkyl, $(CH_2)_qC_{3-7}$cycloalkyl, $(CH_2)_q$aryl, $(CH_2)_q$heterocyclyl, CHO, $C(O)C_{1-6}$alkyl, $C(O)(CH_2)_qC_{3-7}$cycloalkyl, $C(O)(CH_2)_q$aryl, $C(O)(CH_2)_q$heterocyclyl, $C(O)(CH_2)_pNR^aR^b$, $(CH_2)_qCO_2C_{1-6}$alkyl, $CO_2(CH_2)_qC_{3-7}$cycloalkyl, $CO_2(CH_2)_q$aryl, $CO_2(CH_2)_q$heterocyclyl, $CO_2(CH_2)_pNR^aR^b$, $(CH_2)_pNR^aCOR^b$, $(CH_2)_pNR^aCO_2R^b$, $(CH_2)_qCONR^a$aryl or $(CH_2)_qCONR^a$-heterocyclyl where $R^a$ and $R^b$ are as previously defined;

or $R^{11}$ and $R^{12}$, together with the nitrogen atom to which they are attached, represent a ring selected from the group consisting of:

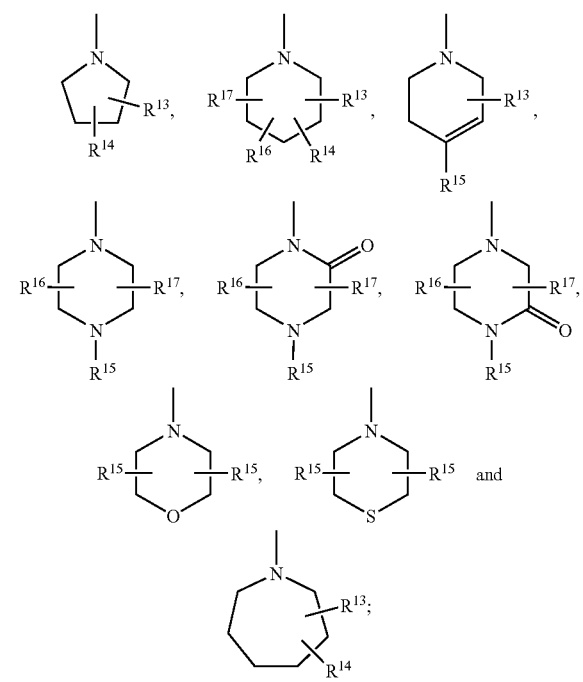

$R^{13}$ and $R^{14}$ each independently represent hydrogen, halogen, hydroxy, $C_{1-6}$alkyl, $C_{2-6}$alkenyl, $C_{2-6}$alkynyl, hydroxy$C_{1-6}$alkyl, fluoro$C_{1-6}$alkyl, $C_{1-6}$alkoxy, $(CH_2)_qC_{3-7}$cycloalkyl, $(CH_2)_q$aryl, $(C_{2-6}$alkenyl)aryl, $(C_{2-6}$alkynyl)

aryl, $(CH_2)_q$heterocyclyl, $(CH_2)_qNR^aR^b$, $O(CH_2)_qC_{3-7}$cycloalkyl, $O(CH_2)_q$aryl, $O(CH_2)_q$heterocyclyl, $O(CH_2)_p$$NR^aR^b$, $OC(O)C_{1-6}$alkyl, $C(O)C_{1-6}$alkyl, $C(O)(CH_2)_q$aryl, $C(O)(CH_2)_q$heterocyclyl, $C(O)(CH_2)_qNR^aR^b$, $CO_2H$, $CO_2C_{1-6}$alkyl, $CO_2(CH_2)_qC_{3-7}$cycloalkyl, $CO_2(CH_2)_q$aryl, $CO_2(CH_2)_q$heterocyclyl or $CO_2(CH_2)_pNR^aR^b$, where $R^a$ and $R^b$ are as previously defined;

or, when they are attached to the same carbon atom, $R^{13}$ and $R^{14}$ may together represent =O, =CHCO$_2$R$^a$, —O(CH$_2$)$_m$O—, —CH$_2$O(CH$_2$)$_s$—, —CH$_2$OCH$_2$C(O)—, —CH$_2$OCH$_2$CH(OH)—, —CH$_2$OCH$_2$C(CH$_3$)$_2$—, —CH$_2$OC(CH$_3$)$_2$CH$_2$—, —C(CH$_3$)$_2$OCH$_2$CH$_2$—, —CH$_2$C(O)OCH$_2$—, —OC(O)CH$_2$CH$_2$—, —C(O)OCH$_2$CH$_2$—, —C(O)OC(CH$_3$)$_2$CH$_2$—, —C(O)OCH$_2$C(CH$_3$)$_2$—, —OCH$_2$(CH$_2$)$_s$—, —OC(CH$_3$)$_2$CH$_2$CH$_2$—, —OCH$_2$C(CH$_3$)$_2$CH$_2$—, —OCH$_2$CH$_2$C(CH$_3$)$_2$—, —OCH$_2$CH=CHCH$_2$—, —OCH$_2$CH(OH)CH$_2$CH$_2$—, —OCH$_2$CH$_2$CH(OH)CH$_2$—, —OCH$_2$C(O)CH$_2$CH$_2$—, —OCH$_2$CH$_2$C(O)CH$_2$—, or a group of the formula

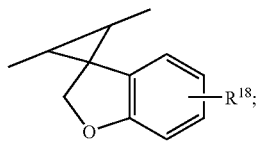

or, where they are attached to adjacent carbon atoms, $R^{13}$ and $R^{14}$ may together represent —OCH$_2$CH$_2$— or —OCH$_2$CH(OH)—, or $R^{13}$ and $R^{14}$ may together form a fused benzene ring;

or, $R^{13}$ and $R^{14}$ together form a $C_{1-2}$alkylene bridge across the pyrrolidine, piperidine or hexamethyleneimine ring to which they are attached;

$R^{15}$ represents hydrogen, $C_{1-6}$alkyl, $(CH_2)_qC_{3-7}$cycloalkyl, $(CH_2)_q$aryl, $(CH_2)_q$heterocyclyl, CHO, $C(O)C_{1-6}$alkyl, $C(O)(CH_2)_qC_{3-7}$cycloalkyl, $C(O)(CH_2)_q$aryl, $C(O)(CH_2)_q$heterocyclyl, $CO_2C_{1-6}$alkyl, $CO_2(CH_2)_qC_{3-7}$cycloalkyl, $CO_2(CH_2)_q$aryl, $CO_2(CH_2)_q$heterocyclyl or $CO_2(CH_2)_pNR^aR^b$, where $R^a$ and $R^b$ are as previously defined;

or, where they are attached to adjacent carbon atoms, $R^{15}$ and $R^{16}$ may together form a fused imidazolyl or triazolyl ring;

$R^{16}$ and $R^{17}$ each independently represent hydrogen, halogen, hydroxy, $C_{1-6}$alkyl or oxo (=O);

$R^{18}$ represents hydrogen, halogen, hydroxy, $C_{1-4}$alkyl, hydroxy$C_{1-4}$alkyl or fluoro$C_{1-4}$alkyl;

d is zero, 1, 2 or 3;

n is zero, 1 or 2;

m D is 1 or 2;

p is 1, 2, 3 or 4;

q is zero, 1, 2, 3 or 4; and s is 1, 2 or 3;

and pharmaceutically acceptable salts and N-oxides thereof.

A preferred class of compound of formula (I) is that wherein $R^1$ is hydroxy, $C_{1-6}$alkyl, fluoro$C_{1-6}$alkyl, $C_{2-6}$alkenyl, $C_{1-6}$alkoxy, fluoro$C_{1-6}$alkoxy, $C_{2-6}$alkenyloxy, $C_{3-7}$cycloalkoxy, $C_{3-7}$cycloalkyl$C_{1-4}$alkoxy, cyano, $NR^aR^b$, $SR^a$, $OSO_2R^a$, or $R^1$ together with the group $R^2$ form a 5-membered saturated ring containing one oxygen atom.

A particularly preferred class of compound of formula (I) is that wherein $R^1$ is $C_{1-6}$alkyl, fluoro$C_{1-6}$alkyl, $C_{1-6}$alkoxy, fluoro$C_{1-6}$alkoxy, $C_{3-7}$cycloalkoxy or $C_{3-7}$cycloalkoxy$C_{1-4}$alkyl, especially methyl, trifluoromethyl, methoxy, trifluoromethoxy, 2,2,2-trifluoroethoxy, difluoromethoxy, cyclopropoxy or cyclopropylmethoxy.

Another preferred class of compound of formula (I) is that wherein $R^2$ is a hydrogen, fluorine or chlorine atom, especially a hydrogen atom.

A further preferred class of compound of formula (I) is that wherein $R^3$ is hydrogen, halogen, fluoro$C_{1-6}$alkyl, fluoro$C_{1-6}$alkoxy, cyano, $NR^aR^b$, $NR^aCOR^d$ (where $R^d$ is methyl, methoxy, trifluoromethyl or phenyl), or a 5-membered aromatic heterocyclic group as previously defined.

Also preferred is the class of compounds of formula (I) in which $R^3$ is $C_{1-6}$alkyl, fluoro$C_{1-6}$alkyl, fluoro$C_{1-6}$alkoxy or a 5-membered aromatic heterocyclic group as previously defined, especially methyl, trifluoromethyl, trifluoromethoxy or 5-trifluoromethyl-1,2,3,4-tetrazol-1-yl.

Preferably $R^1$ and $R^3$ are in the 3 and 5 positions of the phenyl ring.

More preferably $R^1$ is 3-fluoro or 3-CF$_3$.

More preferably $R^3$ is 5-fluoro or 5-CF$_3$.

More preferably $R^2$ is hydrogen.

Most preferably $R^1$ is 3-CF$_3$, $R^2$ is hydrogen and $R^3$ is 5-CF$_3$.

Another preferred class of compounds of formula (I) is that wherein $R^1$ and $R^3$ are in the 2- and 5-positions of the phenyl ring.

In this sub-class of compounds of formula (I), $R^1$ is preferably $C_{1-6}$alkoxy or $C_{3-7}$cycloalkoxy, especially methoxy or cyclopropoxy.

Also in this sub-class of compounds of formula (I), $R^2$ is preferably hydrogen.

Also, in this sub-class of compounds of formula (I) $R^3$ is preferably hydrogen, $C_{1-6}$alkoxy, fluoro$C_{1-6}$alkoxy or a 5-membered aromatic heterocyclic group as previously defined. Most especially, $R^3$ is hydrogen, methoxy or trifluoromethoxy.

A further preferred class of compound of formula (I) is that wherein $R^4$ is hydrogen.

Another preferred class of compound of formula (I) is that wherein $R^5$ is hydrogen, fluorine, chlorine or CF$_3$, especially hydrogen or fluorine.

Preferably $R^4$ is hydrogen and $R^5$ is hydrogen or 4-fluoro.

Another further preferred class of compounds of formula (I) is that wherein $R^6$ is hydrogen.

Another preferred class of compound of formula (I) is that in which $R^9$ and $R^{10}$ each represents hydrogen.

A further preferred class of compound of formula (I) is that wherein $R^7$ is —$(CH_2)_nNR^{11}R^{12}$ or wherein $R^6$ and $R^7$ together represent =O or —O(CH$_2$)$_m$O— wherein m is as previously defined.

A further preferred class of compound of formula (I) is that wherein $R^{11}$ represents hydrogen, $C_{1-6}$alkyl, $C_{2-6}$alkenyl, hydroxy$C_{1-6}$alkyl, $(CH_2)_qC_{3-7}$cycloalkyl, $(CH_2)_q$aryl, $(CH_2)_q$heterocyclyl, $C(O)C_{1-6}$alkyl, $C(O)(CH_2)_q$aryl, $C(O)(CH_2)_q$heterocyclyl, $C(O)(CH_2)_pNR^aR^b$, $(CH_2)_qCO_2C_{1-6}$alkyl, $(CH_2)_pNR^aCO_2R^b$ or $(CH_2)_qCONR^a$aryl;

and $R^{12}$ represents hydrogen, $C_{1-6}$alkyl, $(CH_2)_qC_{3-7}$cycloalkyl or $CO_2C_{1-6}$alkyl;

or $R^{11}$ and $R^{12}$ together with the nitrogen atom to which they are attached represent a ring selected from the group consisting of

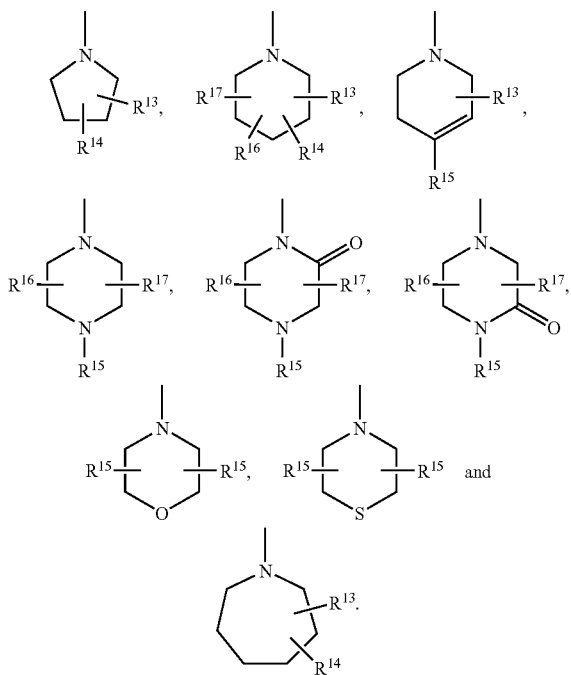

A further preferred class of compounds of formula (I) is that wherein $R^{13}$ represents hydrogen, hydroxy, $C_{1-6}$alkyl, $C_{2-6}$alkenyl, $C_{2-6}$alkynyl, hydroxy$C_{1-6}$alkyl, fluoro$C_{1-6}$alkyl, $(C_{2-6}$alkynyl)aryl, $(CH_2)_q$aryl, $(CH_2)_q$heterocyclyl, $(CH_2)_qNR^aR^b$, $OC(O)C_{1-6}$alkyl, $C(O)(CH_2)_qNR^aR^b$, $CO_2H$ or $CO_2C_{1-6}$alkyl;

and $R^{14}$ represents hydrogen, halogen, hydroxy, $C_{1-6}$alkyl or $(CH_2)_qNR^aR^b$;

or when they are attached to the same carbon atom, $R^{13}$ and $R^{14}$ may together represent =O, —O(CH$_2$)$_m$O—, —CH$_2$O(CH$_2$)$_s$—, —CH$_2$OCH$_2$C(O)—, —CH$_2$OCH$_2$CH(OH)—, —CH$_2$OCH$_2$C(CH$_3$)$_2$—, —CH$_2$OC(CH$_3$)$_2$CH$_2$—, —C(CH$_3$)$_2$OCH$_2$CH$_2$—, —CH$_2$C(O)OCH$_2$—, —OC(O)CH$_2$CH$_2$—, —C(O)OCH$_2$CH$_2$—, —C(O)OC(CH$_3$)$_2$CH$_2$—, —C(O)OCH$_2$C(CH$_3$)$_2$—, —OCH$_2$(CH$_2$)$_s$—, —OC(CH$_3$)$_2$CH$_2$CH$_2$—, —OCH$_2$CH=CHCH$_2$—, —OCH$_2$CH(OH)CH$_2$CH$_2$—, —OCH$_2$CH$_2$CH(OH)CH$_2$—, —OCH$_2$C(O)CH$_2$CH$_2$—, or a group of the formula

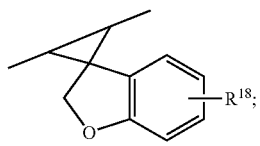

or, when they are attached to adjacent carbon atoms, $R^{13}$ and $R^{14}$ may together represent —OCH$_2$CH$_2$— or —OCH$_2$CH(OH)—, or $R^{13}$ and $R^{14}$ may together form a fused benzene ring;

or $R^{13}$ and $R^{14}$ together form a $C_{1-2}$alkylene bridge across the pyrrolidine or piperidine ring to which they are attached.

A further preferred class of compounds of formula (I) is that wherein $R^{15}$ represents hydrogen, $C_{1-6}$alkyl, $(CH_2)_qC_{3-7}$cycloalkyl, $(CH_2)_q$aryl, $(CH_2)_q$heterocyclyl, CHO, $C(O)C_{1-6}$alkyl, $C(O)C_{3-7}$cycloalkyl, $C(O)(CH_2)_q$aryl or $CO_2C_{1-6}$alkyl.

A yet further preferred class of compounds of formula (I) is that wherein $R^{12}$ represents hydrogen, $C_{1-6}$alkyl, $(CH_2)_q C_{3-7}$cycloalkyl or $CO_2C_{1-6}$alkyl.

A particularly preferred class of compounds of formula (I) is that wherein $R^{11}$ represents $C_{1-6}$alkyl (especially methyl);

and $R^{12}$ represents $C_{1-6}$alkyl (especially methyl);

or $R^{11}$ and $R^{12}$ together with the nitrogen atom to which they are attached represent a ring selected from the group consisting of:

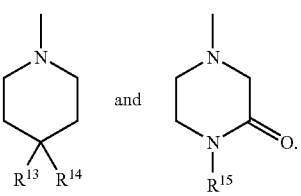

A further particularly preferred class of compounds of formula (I) is that wherein $R^{13}$ and $R^{14}$ together represent =O, —OCH$_2$CH$_2$O—, —OCH$_2$CH$_2$CH$_2$— or —CH$_2$OCH$_2$CH$_2$—.

A yet further particularly preferred class of compounds of formula (I) is that wherein $R^{15}$ represents phenyl.

Another preferred class of compound of formula (I) is that wherein the ring A is a phenyl ring.

A still further preferred class of compounds of formula (I) is that wherein d represents 1 or 2.

Also preferred are those compounds of formula (I) in which $R^8$ represents hydrogen, hydroxy, $C_{1-4}$alkyl or $C_{1-4}$alkoxy, and most especially hydrogen, hydroxy, methyl or methoxy.

Another preferred class of compounds of formula (I) is that wherein n is zero.

A further preferred class of compounds of formula (I) is that wherein m is 2.

Another preferred class of compounds of formula (I) is that wherein p is 1, 2 or 3, particularly 1 or 2, and especially 1.

A further preferred class of compounds of formula (I) is that wherein q is zero, 1 or 2, particularly zero or 1.

One favoured group of compounds of the present invention are of the formula (Ia) and pharmaceutically acceptable salts and N-oxides thereof:

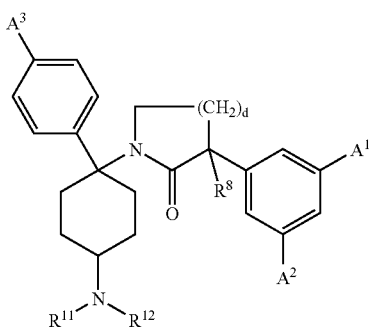

(Ia)

wherein $A^1$ is fluorine or $CF_3$;

$A^2$ is fluorine or $CF_3$;

$A^3$ is fluorine or hydrogen;

d is 1 or 2; and $R^8$, $R^{11}$ and $R^{12}$ are as defined in relation to formula (I).

When any variable occurs more than one time in formula (I) or formula (Ia) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the term "hydroxy$C_{1-6}$alkyl" means a $C_{1-6}$alkyl group in which one or more (in particular 1 to 3, and especially 1) hydrogen atoms have been replaced by hydroxy groups. Particularly preferred are hydroxy$C_{1-3}$alkyl groups, for example, $CH_2OH$, $CH_2CH_2OH$, $CH(CH_3)OH$ or $C(CH_3)_2OH$, and most especially $CH_2OH$.

As used herein, the terms "fluoro$C_{1-6}$alkyl" and fluoro$C_{1-6}$ alkoxy" means a $C_{1-6}$alkyl or $C_{1-6}$alkoxy group in which one or more (in particular, 1 to 3) hydrogen atoms have been replaced by fluorine atoms. Particularly preferred are fluoro$C_{1-3}$alkyl and fluoro$C_{1-3}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$, $OCF_3$ and $OCH_2CF_3$.

The cycloalkyl groups referred to herein may represent, for example, cyclopropyl, cyclobutyl, cyclopentyl or cyclohexyl. A suitable $(CH_2)_qC_{3-7}$cycloalkyl group where q is 1 may be, for example, cyclopropylmethyl or cyclohexylmethyl.

Similarly cycloalkoxy groups referred to herein may represent, for example, cyclopropoxy or cyclobutoxy.

As used herein, the terms "alkenyl" and "alkynyl" as a group or part of a group means that the group is straight or branched. Examples of suitable alkenyl groups include vinyl and allyl. A suitable alkynyl group is acetylene or propargyl.

When used herein the term "halogen" means fluorine, chlorine, bromine and iodine. The most apt halogens are fluorine and chlorine of which fluorine is preferred, unless otherwise stated.

As used herein, the term "aryl" as a group or part of a group means an aromatic radical such as phenyl, biphenyl or naphthyl, wherein said phenyl, biphenyl or naphthyl group may be optionally substituted by one, two or three groups independently selected from halogen, $C_{1-6}$alkyl, $C_{1-6}$alkoxy, fluoro$C_{1-6}$alkyl, fluoro$C_{1-6}$alkoxy, $NO_2$, cyano, $SR^a$, $SOR^a$, $SO_2R^a$, $COR^a$, $CO_2R^a$, $CONR^aR^b$, $C_{2-6}$alkenyl, $C_{2-6}$alkynyl, $C_{1-4}$alkoxy$C_{1-4}$alkyl or $—O(CH_2)_mO—$. Preferably said phenyl, biphenyl or naphthyl group is optionally substituted by one or two substituents, especially none or one. Particularly preferred substituents include fluorine, chlorine, bromine, $C_{1-4}$alkyl (especially methyl), $C_{1-4}$alkoxy (especially methoxy), trifluoromethyl, trifluormethoxy or vinyl.

As used herein, the term "heterocyclyl" as a group or part of a group means a saturated, partially saturated or unsaturated heteroatom-containing ring-shaped radical, where the heteroatoms may be selected from nitrogen, oxygen and sulfur. Examples of saturated heterocyclyl radicals include N-linked saturated 3 to 6-membered heteromonocyclic groups containing 1 to 3 nitrogen atoms and optionally 1 oxygen or sulfur atom (for example, azetidinyl, pyrrolidinyl, piperidinyl, morpholinyl, thiomorpholinyl, piperazinyl or piperazinyl substituted on the nitrogen atom by a $C_{1-4}$alkyl group or a $C_{2-4}$alkyl group substituted by hydroxy or $C_{1-2}$alkoxy). Examples of saturated heterocyclyl radicals also include C-linked saturated 3 to 6-membered heteromonocyclic groups containing, for example, one oxygen atom (for instance, tetrahydrofuranyl or tetrahydropyranyl). Examples of partially saturated heterocyclyl radicals include N-linked partially saturated 3 to 6-membered heteromonocyclic groups containing 1 to 3 nitrogen atoms (for example, 3-pyrroline). Examples of unsaturated heterocyclyl radicals include heteroaromatic rings selected from pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indolyl, benzofuranyl, benzthiophenyl, benzimidazolyl, benzisoxazolyl, benzoxazolyl, benzthiazolyl or benzisothiazolyl.

Said saturated and partially saturated heterocyclyl radicals may be optionally substituted by one, two or three groups independently selected from halogen, $C_{1-6}$alkyl, $C_{1-6}$alkoxy, fluoro$C_{1-6}$alkyl, fluoro$C_{1-6}$alkoxy, $NO_2$, cyano, oxo (=O), $NR^aR^b$, $SR^a$, $SOR^a$, $SO_2R^a$, $COR^a$, $CO_2R^a$, $CONR^aR^b$, $C_{2-6}$alkenyl, $C_{2-6}$alkynyl, $C_{1-4}$alkoxy$C_{1-4}$alkyl, $—O(CH_2)_mO—$, $—OCH_2CH_2CH_2—$, $—CH_2OCH_2CH_2—$ or $—CH_2OCH_2C(O)—$. Preferably said saturated or partially saturated heterocyclyl radical is optionally substituted by one or two substituents, especially none or one. Particularly preferred substituents include fluorine, chlorine, bromine, $C_{1-4}$alkyl (especially methyl), $C_{1-4}$alkoxy (especially methoxy), trifluoromethyl, trifluoromethoxy, oxo, vinyl, $C_{1-4}$alkylamino (especially methylamino) or di($C_{1-4}$alkyl) amino (especially dimethylamino).

Said unsaturated heterocyclyl radicals may be optionally substituted by one, two or three groups independently selected from halogen, $C_{1-6}$alkyl, $C_{1-6}$alkoxy, fluoro$C_{1-6}$alkyl, fluoro$C_{1-6}$alkoxy, $NO_2$, cyano, $NR^aR^b$, $SR^a$, $SOR^a$, $SO_2R^a$, $COR^a$, $CO_2R^a$, $CONR^aR^b$, $C_{2-6}$alkenyl, $C_{2-6}$alkynyl, $C_{1-4}$alkoxy$C_{1-4}$alkyl or $—O(CH_2)_mO—$. Preferably said unsaturated heterocyclyl is optionally substituted by one or two substituents, especially none or one. Particularly preferred substituents include fluorine, chlorine, bromine, $C_{1-4}$alkyl (especially methyl), $C_{1-4}$alkoxy (especially methoxy), trifluoromethyl, trifluoromethoxy or vinyl.

As used herein, the term "carbocyclyl" as a group or part of a group means a 3 to 7-membered cycloalkyl radical such as cyclopropyl, cyclobutyl, cyclopentyl or cyclohexyl, wherein said cycloalkyl radical may be optionally substituted by one, two or three groups independently selected from halogen, $C_{1-6}$alkyl, $C_{1-6}$alkoxy, hydroxy$C_{1-6}$alkyl, fluoro$C_{1-6}$alkyl, fluoro$C_{1-6}$alkoxy, $NO_2$, cyano, $SR^a$, $SOR^a$, $SO_2R^a$, $COR^a$, $CO_2R^a$, $CONR^aR^b$, $C_{2-6}$alkenyl, $C_{2-6}$alkynyl, $C_{1-4}$alkoxy$C_{1-4}$alkyl or $—O(CH_2)_mO—$. Preferably said cycloalkyl radical is substituted by one or two substituents, especially one. Particularly preferred substituents include fluorine, chlorine, bromine, $C_{1-4}$alkyl (especially methyl), methoxy, hydroxy$C_{1-4}$alkyl (especially $C(CH_3)_2OH$), trifluoromethyl, trifluoromethoxy or vinyl.

Specific compounds within the scope of this invention include:

(RS)-3-[3,5-bis(trifluoromethyl)phenyl]-1-(1,4-dioxa-8-phenylspiro[4.5]decan-8-yl)-2-piperidinone;

(RS)-3-[3,5-bis(trifluoromethyl)phenyl]-1-(1,4-dioxa-8-phenylspiro[4.5]decan-8-yl)-2-pyrrolidinone;

(RS)-3-hydroxy-[3,5-bis(trifluoromethyl)phenyl]-1-(1,4-dioxa-8-phenylspiro[4.5]decan-8-yl)-2-pyrrolidinone;

(RS)-3-methyl-[3,5-bis(trifluoromethyl)phenyl]-1-(1,4-dioxa-8-phenylspiro-[4.5]decan-8-yl)-2-pyrrolidinone;

(RS)-3-[3,5-bis(trifluoromethyl)phenyl]-1-(4-oxo-1-phenylcyclohexyl)-2-piperidinone;

(RS)-3-[3,5-bis(trifluoromethyl)phenyl]-1-(4-oxo-1-phenylcyclohexyl)-2-pyrrolidinone;
(RS)-3-hydroxy-3-[3,5-bis(trifluoromethyl)phenyl]-1-(4-oxo-1-phenylcyclohexyl)-2-pyrrolidinone;
(RS)-3-methyl-3-[3,5-bis(trifluoromethyl)phenyl]-1-(1,4-dioxa-8-phenylspiro[4.5]decan-8-yl)-2-pyrrolidinone;
cis-(RS)-3-[3,5-bis(trifluoromethyl)phenyl]-1-[4-(2-oxa-8-azaspiro[4.5]decan-8-yl)-1-phenylcyclohexyl]-2-piperidinone;
trans-(RS)-3-[3,5-bis(trifluoromethyl)phenyl]-1-(2-oxa-8-azaspiro[4.5]decan-8-yl)-1-phenylcyclohexyl]-2-piperidinone;
trans-(RS)-3-[3,5-bis(trifluoromethyl)phenyl]-1-(4-dimethylamino-1-phenylcyclohexyl)-2-pyrrolidinone;
trans-(RS)-3-hydroxy-3-[3,5-bis(trifluoromethyl)phenyl]-1-[4-(2-oxa-8-azaspiro[4.5]decan-8-yl)-1-phenylcyclohexyl]-2-piperidinone;
trans-(RS)-3-methoxy-3-[3,5-bis(trifluoromethyl)phenyl]-1-[4-(2-oxa-8-azaspiro[4.5]decan-8-yl)-1-phenylcyclohexyl]-2-piperidinone; and
trans-(RS)-3-methyl-3-[3,5-bis(trifluoromethyl)phenyl]-1-[4-(2-oxa-8-azaspiro[4.5]decan-8-yl)-1-phenylcyclohexyl]-2-piperidinone;
and pharmaceutically acceptable salts and N-oxides thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have one or more asymmetric centres, and may accordingly exist both as enantiomers and as diastereoisomers. It is to be understood that all such isomers and mixtures thereof are encompassed within the scope of the present invention.

The preferred compounds of the formula (I) and (Ia) will have the stereochemistry of the 1- and 4-positions as shown in formula (Ib)

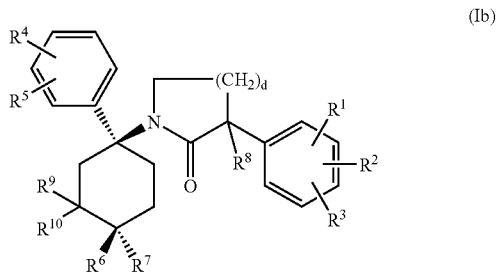

(Ib)

It will be appreciated that the preferred definitions of the various substituents recited herein may be taken alone or in combination and, unless otherwise stated, apply to the generic formula for compounds of the present invention as well as to the preferred classes of compound represented by formula (Ia) and formula (Ib).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation. Oral compositions such as tablets, pills, capsules or wafers are particularly preferred.

A more detailed description of pharmaceutical compositions that are suitable for the formulation of compounds of the present invention is disclosed in U.S. Pat. No. 6,071,927, the content of which is incorporated herein by reference (see in particular, column 8, line 50 to column 10, line 4).

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. A comprehensive listing of clinical conditions, uses and methods of treatment for which the compounds of the present invention will be useful is disclosed in U.S. Pat. No. 6,071,927, the content of which is incorporated herein by reference (see, in particular, column 10, line 14 to column 22, line 18).

In particular, the compounds of the present invention are useful in the treatment of a variety of psychiatric disorders or disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; and anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders.

The compounds of the present invention are also particularly useful in the treatment of nociception and pain. Diseases and conditions in which pain predominates include soft tissue and peripheral damage, such as acute trauma, osteoarthritis, rheumatoid arthritis, musculo-skeletal pain, particularly after trauma, spinal pain, myofascial pain syndromes, headache, migraine, episiotomy pain, and burns.

The compounds of the present invention are also particularly useful in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; in the treatment of inflammatory diseases such as inflammatory bowel disease, psoriasis, fibrositis, osteoarthritis, rheumatoid arthritis, pruritis and sunburn; and in the treatment of allergic disorders such as eczema and rhinitis.

The compounds of the present invention are also particularly useful in the treatment of gastrointestinal (GI) disorders, including inflammatory disorders and diseases of the GI tract such as ulcerative colitis, Crohn's disease and irritable bowel syndrome.

The compounds of the present invention are also particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy; by radiation including radiation therapy such as in the treatment of cancer; and in the treatment of post-operative nausea and vomiting.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

In the treatment of psychiatric disorders, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A), compounds of formula (I) in which $R^6$ is hydrogen and $R^7$ is a group of the formula $NR^{11}R^{12}$, may be prepared by the interconversion of a compound of formula (I) in which $R^6$ and $R^7$ together represent =O, hereinafter a compound of formula (II)

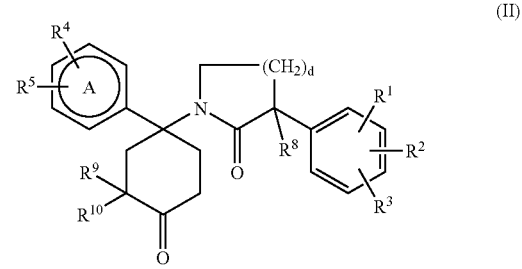

(II)

in which $R^1$, $R^2$, $R^3$, $R^4$, $R^5$, $R^8$, $R^9$, $R^{10}$, ring A and d are as defined above, by reaction with an amine of the formula $HNR^{11}R^{12}$ in the presence of a reducing agent.

Suitable reducing agents of use in this reaction include, for example, sodium cyanoborohydride and sodium triacetoxyborohydride. The reaction may also be carried out in the presence of a Lewis acid such as zinc chloride.

The reaction is conveniently effected in a suitable solvent such as an alcohol, for example, methanol, or a halogenated hydrocarbon, for example, 1,2-dichloroethane, or a mixture thereof, at a temperature between 0° C. and 50° C., conveniently at about room temperature.

According to another general process (B), compounds of formula (I) in which $R^6$ and $R^7$ together form a group $-O(CH_2)_mO-$, wherein m is as defined above, may be prepared by cyclising a compound of formula (III):

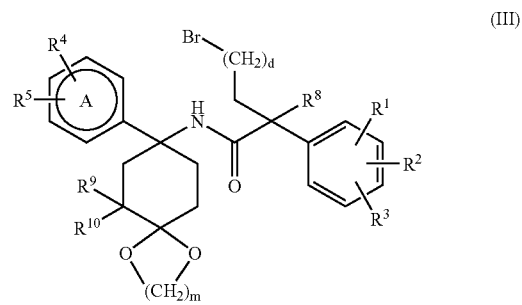

(III)

in which $R^1$, $R^2$, $R^3$, $R^4$, $R^5$, $R^8$, $R^9$, $R^{10}$, ring A, d and m are as defined above.

The reaction is typically carried out in the presence of an inorganic base, such as sodium hexamethyldisilazide or sodium hydride, and in a solvent, such as an ether, for example tetrahydrofuran.

The resulting compound of formula (I) may be subjected to interconversion reactions to prepare further compounds of formula (I) in which $R^6$ and $R^7$ are as defined above.

In an alternative general process (C), compounds of formula (I) in which $R^6$ and $R^7$ together form a group —O(CH$_2$)$_m$O—, wherein m is as defined above, may be prepared by cyclising a compound of formula (IV):

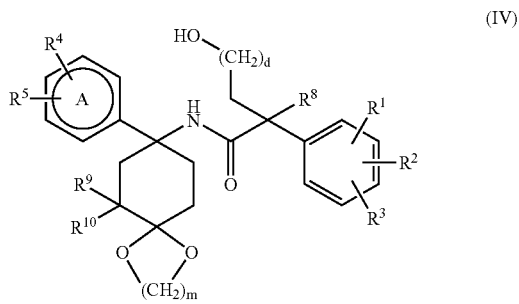

(IV)

in which $R^1$, $R^2$, $R^3$, $R^4$, $R^5$, $R^8$, $R^9$, $R^{10}$, ring A, d and m are as defined above.

The reaction is typically carried out in the presence of a mesylating agent, such as methylsulphonyl chloride, an organic base, such as sodium hexamethyldisilylazide and in a solvent, such as an ether, for example tetrahydrofuran.

The resulting compound of formula (I), may be subjected to interconversion reactions to prepare further compounds of formula (I) in which $R^6$ and $R^7$ are as defined above.

According to another general process (D), compounds of formula (I) in which $R^6$ and $R^7$ together represent =O, i.e. compounds of formula (II) may be prepared by the interconversion of a compound of formula (I) in which $R^6$ and $R^7$ together form a group —O(CH$_2$)$_m$O—, wherein m is as defined above, hereinafter referred to as a compound of formula (V)

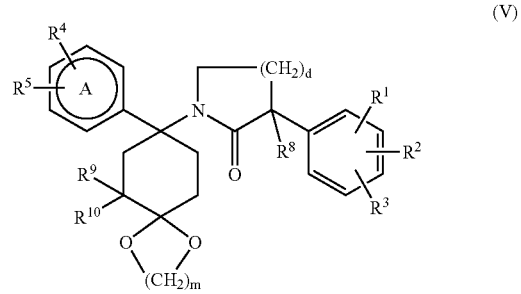

(V)

in which $R^1$, $R^2$, $R^3$, $R^4$, $R^5$, $R^8$, $R^9$, $R^{10}$, ring A, d and m are as defined above.

The reaction is typically effected in the presence of a mineral acid such as hydrochloric acid in a suitable solvent such as acetone at a temperature between room temperature and 70° C., for example, at about 50° C.

Interconversion reactions to modify the substituent $R^7$ may be effected using conventional procedures, for example as shown in the following Scheme 1. The methods depicted in Scheme 1 are not exhaustive and illustrate just some of the possible routes to further compounds of formula (I) (for convenience, only the bottom part of the formulae is drawn).

Scheme 1

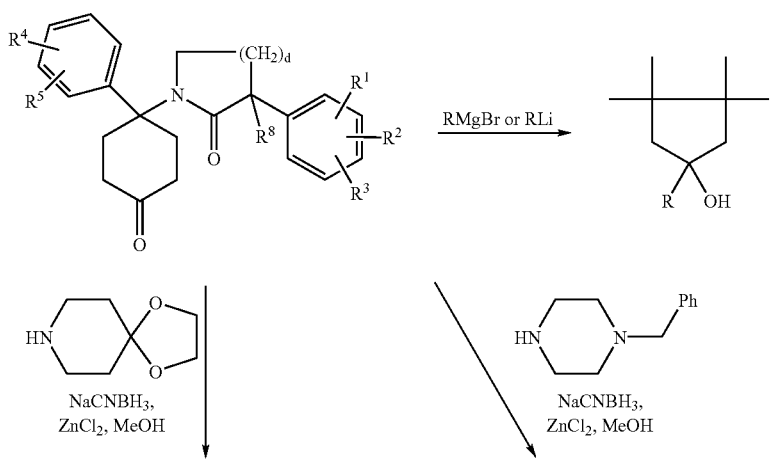

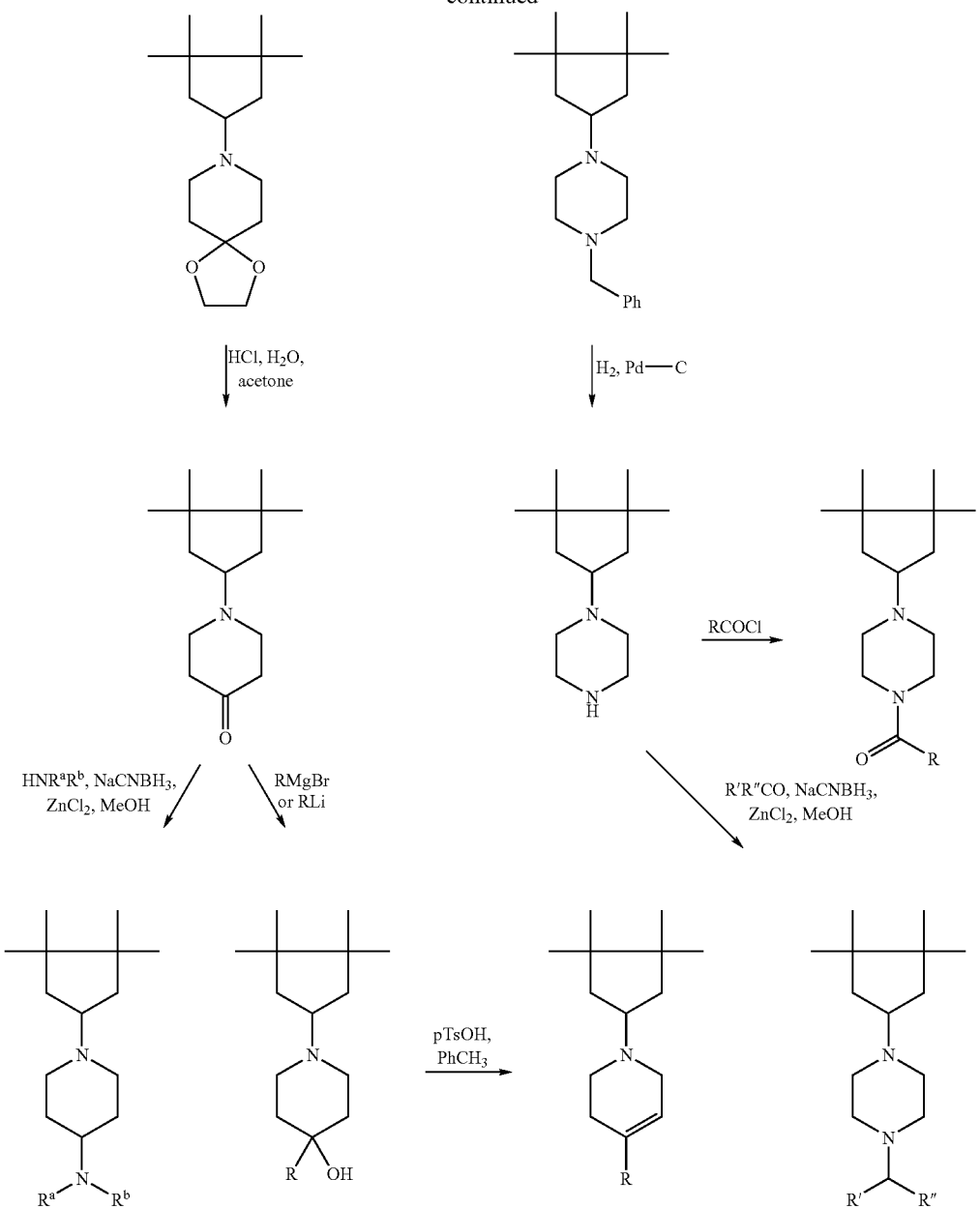

In the above Scheme 1, the groups designated as R, R' and R" take on any of the definitions of $R^{13}$, $R^{14}$ or $R^{15}$, where appropriate.

Substituent groups $R^9$ and $R^{10}$ may be added to the intermediates involved in production of the compounds of formula (I) in the later stages of the reaction procedures. Such addition may take place using conventional reagents and conditions.

Further details of suitable procedures for the preparation of compounds of formula (I) will be found in the accompanying Examples.

Compounds of formula (III) and (IV) may be prepared by a variety of methods well known to those skilled in the art. An example of suitable routes to the compounds of formula (III) is shown in the following Schemes 2 and 3, and to the compounds of formula (IV) in Scheme 4.

Scheme 2

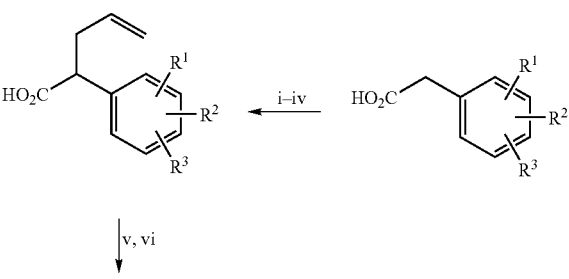

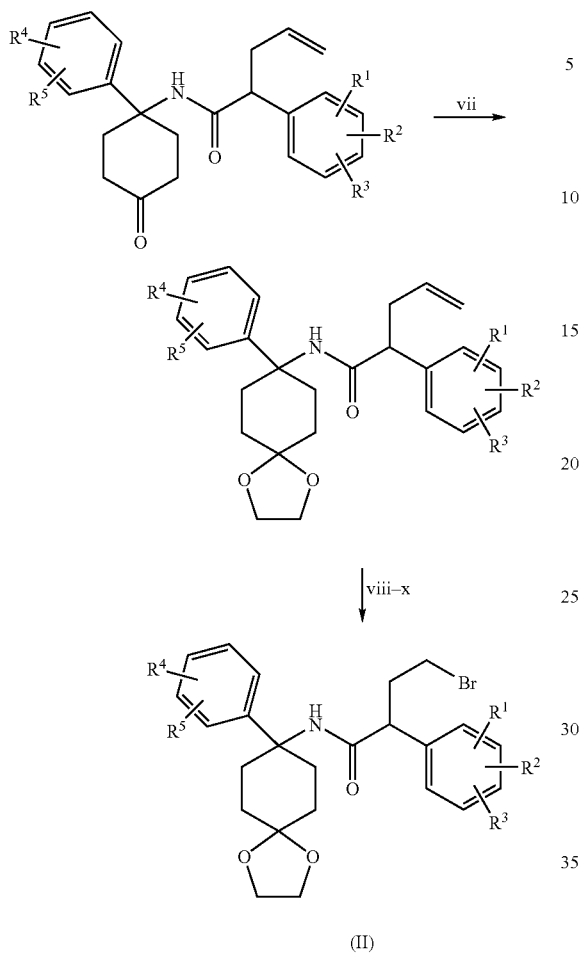

Appropriate reagents for each of the steps (i) to (x) in Scheme 2 may be as follows:
(i) nBuLi;
(ii) BrCH$_2$CH=CH$_2$;
(iii) dicyclohexylamine, Py;
(iv) citric acid, EtOAc, H$_2$O;
(v) (COCl)$_2$, DMF, CH$_2$Cl$_2$;
(vi) 4-oxo-1-phenylcyclohexylamine, Py;
(vii) HOCH$_2$CH$_2$OH, pTsOH, PhCH$_3$;
(viii) O$_3$;
(ix) NaBH$_4$; and
(x) CBr$_4$, Ph$_3$P, Py.

Appropriate reagents for each of the steps (i) to (x) in Scheme 3 may be as follows:
(i) nBuLi;
(ii) BrCH$_2$CH$_2$CH=CH$_2$;
(iii) dicyclohexylamine, recrystallise;
(iv) citric acid, EtOAc, H$_2$O;
(v) (COCl)$_2$, DMF, CH$_2$Cl$_2$;
(vi) 4-oxo-1-phenylcyclohexylamine, Py;
(vii) HOCH$_2$CH$_2$OH, pTsOH, PhCH$_3$;
(viii) O$_3$;
(ix) NaBH$_4$; and
(x) CBr$_4$, Ph$_3$P, Py.

Scheme 3

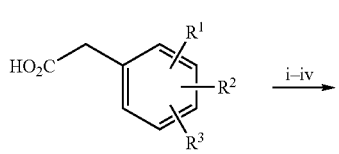

Scheme 4

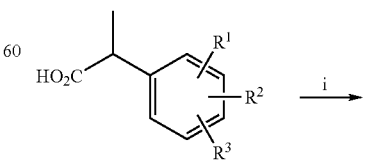

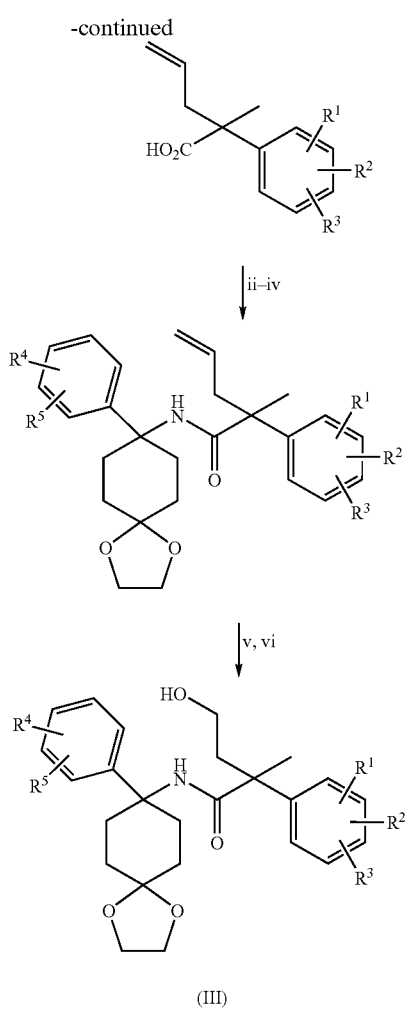

Appropriate reagents for each of the steps (i) to (vi) in Scheme 5 may be as follows:
(i) nBuLi, BrCH$_2$CH=CH$_2$, THF;
(ii) (COCl)$_2$, DMF, CH$_2$Cl$_2$;
(iii) 4-amino-4-phenylcyclohexane, Py, CH$_2$Cl$_2$;
(iv) HOCH$_2$CH$_2$OH, pTsOH, PhCH$_3$;
(v) O$_3$; and
(vi) NaBH$_4$.

The starting materials in each of the above Schemes 2, 3 and 4 are either known compounds or may be prepared by conventional methods, for instance by methods analogous to those described herein.

It will be appreciated that the general methodology described above may be adapted, using methods that are readily apparent to one of ordinary skill in the art, in order to prepare further compounds of the present invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with IC$_{50}$ at the NK$_1$ receptor of less than 100 nM on said test method.

The following non-limiting Examples serve to illustrate the preparation of compounds of the present invention:

Description 1

Dimethyl 4-Oxo-1-phenyl-1,3-cyclohexanedicarboxylic

Sodium hydride (60% in mineral oil, 35.8 g, 1.49 mol) was washed with hexane to remove the mineral oil, suspended in dimethylformamide (400 mL) and cooled to 0° C. Methyl phenyl acetate (42 mL, 0.3 mol) was added slowly with stirring. Methyl acrylate (59 mL, 0.65 mol) was added dropwise over 2 hours at 0° C. and the mixture was stirred at room temperature overnight. Aqueous ammonium chloride (saturated) was added and the mixture was extracted with dichloromethane (2×700 mL). The combined organic fractions were washed with water (5×500 mL), dried (MgSO$_4$) and the solvent was evaporated under reduced pressure. The residue purified by flash column chromatography on silica gel, eluting with isohexane/Et$_2$O (80:20) and the residue was triturated with isohexane-Et$_2$O (50:50). The solid was collected and dried in vacuo to give the title compound as colourless crystals (30 g, 35%). $^1$H NMR (400 Mz, CDCl$_3$) δ 12.11 (1H, s), 7.36-7.25 (5H, m), 3.81 (3H, s), 3.64 (3H, s), 3.08 (1H, d, J 16.1 Hz), 2.73 (1H, d, J 16.1 Hz), 2.26-2.37 (2H, m), and 2.22-2.17 (2H, m).

Description 2

4-Oxo-1-phenylcyclohexanecarboxylic Acid

Lithium hydroxide monohydrate (11.08 g, 264 mmol) was added to a suspension of dimethyl 4-oxo-1-phenyl-1,3-cyclohexanedicarboxylate (Description 1, 25.5 g, 87.9 mmol) in methanol (250 mL), water (83 mL) and tetrahydrofuran (83 mL) and the mixture was heated under reflux for 3 days. The mixture was cooled and the tetrahydrofuran and methanol were evaporated under reduced pressure. The pH was adjusted to 1 with hydrochloric acid (5M) and the mixture was extracted with dichloromethane. The combined organic fractions were dried (MgSO$_4$) and the solvent was evaporated under reduced pressure to give the title compound as a light yellow solid (19 g, 99%). $^1$H NMR (400 MHz, CDCl$_3$) δ 7.50-7.29 (5H, m), 2.29-2.73 (2H, m), 2.62-2.55 (2H, m), 2.47-2.41 (2H, m), and 2.35-2.27 (2H, m).

Description 3

4-Oxo-1-phenylcyclohexylamine Hydrochloride

Diphenylphosphoryl azide (18.8 mL, 23.9 g, 87 mmol) was added to a solution of 4-oxo-1-phenylcyclohexanecarboxylic acid (Description 2, 17.1 g, 78 mmol) and triethylamine (24.4 mL, 17.7 g, 175 mmol) in toluene (260 mL) and the mixture was stirred at 90° C. for 90 minutes. The mixture was cooled, diluted with ethyl acetate (300 mL) and washed with sodium carbonate (2×250 mL). The combined aqueous fractions were extracted with ethyl acetate (300 mL) and the combined organic fractions were washed with brine (250 mL), dried (MgSO$_4$) and the solvent was evaporated under reduced pressure. The residue was suspended in hydrochloric acid (5M, 500 mL) and the mixture was heated under reflux for 2 hours. The mixture was cooled, the solvent was evaporated under reduced pressure and the residue was dried azeotropically by evaporating toluene under reduced pressure (4×) to give crude title compound which was used without further purification. m/z (ES$^+$) 190 (M+1)

Description 4

Dicyclohexylammonium (RS)-α-Methyl-3,5-bis(trifluoromethyl)benzeneacetate n-Butyllithium (2.5M solution in hexanes, 67.6 mL, 169 mmol) was added slowly to a stirred, cooled (−78° C.) solution of 3,5-bis(trifluoromethyl)benzeneacetic acid (20.0 g, 73.5 mmol) in tetrahydrofuran (400 mL) and the mixture was stirred at −78° C. for 1 hour. Iodomethane (6.87 mL, 110 mmol) was added slowly and the mixture was allowed to warm to room temperature and stirred overnight. Aqueous sodium bisulfite (20%) was added until the mixture was acidic. The mixture was extracted with ethyl acetate, the combined organic fractions were dried (MgSO$_4$) and the solvent was evaporated under reduced pressure. The residue was dissolved in ethyl acetate (400 mL), dicyclohexylamine (10 mL, 80.85 mmol) was added and the mixture was heated under reflux for 1 hour. The mixture was cooled and the solid was collected and dried in vacuo to give the title compound as a colourless solid (31.13 g, 91%). $^1$H NMR (400 MHz, CDCl$_3$) δ 7.83 (2H, s), 7.68 (1H, s), 3.66 (1H, q, J 7.1 Hz), 2.83-2.75 (2H, m), 1.87-1.84 (4H, m), 1.71-1.68 (4H, m), 1.60-1.57 (2H, m), 1.48 (3H, d, J 7.1 Hz), 1.28-1.08 (8H, m), and 1.03-0.92 (2H, m).

Description 5

Dicyclohexylammonium (RS)-α-(3-Butenyl)-3,5-bis(trifluoromethyl)benzeneacetate

Prepared from 3,5-bis(trifluoromethyl)benzeneacetic acid and 4-bromo-1-butene according to the method of Description 4. $^1$H NMR (400 MHz, CDCl$_3$) δ 7.85 (2H, s), 7.69 (1H, s), 5.86-5.75 (1H, s), 5.00-4.95 (2H, m), 3.51 (1H, t, J 7.5 Hz), 2.84-2.77 (2H, m), 2.24-2.15 (1H, m), 2.08-1.99 (2H, m), 1.87 (4H, d, J 10 Hz), 1.82-1.73 (1H, m), 1.69 (4H, d, J 13 Hz), 1.58 (4H, d, J 13 Hz), 1.30-1.08 (8H, m), and 1.00-0.93 (2H, m).

Description 6

Dicyclohexylammonium (RS)-α-(2-Propenyl)-3,5-bis(trifluoromethyl)benzeneacetate

Prepared from 3,5-bis(trifluoromethyl)benzeneacetic acid and 3-bromo-1-propene according to the method of Description 4. $^1$H NMR (400 MHz, CD$_3$OD) δ 7.95 (2H, s), 7.75 (1H, s), 5.82-5.70 (1H, m), 5.01 (1H, br d, J 17 Hz), 4.93 (1H, br d, J 10 Hz,), 3.65 (1H, t, J 7 Hz), 3.20-3.10 (2H, m), 2.87-2.77 (1H, m), 2.53-2.43 (1H, m), 2.10-2.00 (4H, m), 1.90-1.80 (4H, m), 1.75-1.65 (2H, m), and 1.45-1.12 (10H, m).

Description 7

(RS)-α-Methyl-3,5-bis(trifluoromethyl)benzeneacetic Acid

Dicyclohexylammonium (RS)-α-methyl-3,5-bis(trifluoromethyl)benzeneacetate (Description 4, 31.13 g, 67 mmol) was suspended in ethyl acetate and washed with aqueous citric acid (25%) and water, dried (MgSO$_4$) and the solvent was evaporated under reduced pressure to give the title compound as a colourless solid (19.0 g, 100%). $^1$H NMR (400 MHz, CDCl$_3$) δ 7.81 (1H, s), 7.78 (2H, s), 3.90 (1H, q, J 7.2 Hz), and 1.60 (3H, d, J 7.2 Hz).

Description 8

(RS)-α-(3-Butenyl)-3,5-bis(trifluoromethyl)benzeneacetic Acid

Prepared from dicyclohexylammonium (RS)-α-(3-butenyl)-3,5-bis(trifluoromethyl)benzeneacetate (Description 5) according to the method of Description 7. $^1$H NMR (400 MHz, CDCl$_3$) δ 7.81 (1H, s), 7.78 (2H, s), 5.80-5.70 (1H, s), 5.05-4.98 (2H, m), 3.78-3.73 (1H, m), 2.32-2.23 (1H, m), 2.11-2.00 (2H, m), and 1.96-1.85 (1H, m).

Description 9

(RS)-α-(2-Propenyl)-3,5-bis(trifluoromethyl)benzeneacetic Acid

Prepared from dicyclohexylammonium (RS)-α-(2-propenyl)-3,5-bis(trifluoromethyl)benzeneacetate (Description 6) according to the method of Description 7. $^1$H NMR (400 MHz, CDCl$_3$) δ 7.81 (1H, s), 7.78 (2H, s), 5.68 (1H, m), 5.15-5.05 (2H, m), 3.82 (1H, t, J 7.6 Hz), 2.90 (1H, ddd, J 14, 7, 7 Hz), and 2.58 (1H, ddd, J 14, 7, 7 Hz).

Description 10

(RS)-α-Methyl-α-(2-propenyl)-3,5-bis(trifluoromethyl)benzeneacetic Acid n-Butyllithium (2.5M solution in hexanes, 61.0 mL, 153 mmol) was added slowly to a stirred, cooled (−78° C.) solution of (RS)-α-methyl-3,5-bis(trifluoromethyl)benzeneacetic acid (Description 7, 19.0 g, 66.4 mmol) in tetrahydrofuran (400 mL) and the mixture was stirred at −78° C. for 2 hours. Further n-butyllithium (2.5M solution in hexanes, 8.0 mL, 20 mmol) was added slowly and the mixture was stirred at −78° C. for 20 minutes. Further n-butyllithium (2.5M solution in hexanes, 8.0 mL, 20 mmol) was added slowly and the mixture was stirred at −78° C. for 20 minutes. 3-Bromo-1-propene (8.62 mL, 12.05 g, 100 mmol) was added slowly and the mixture was stirred at −78° C. for 30 minutes, then at room temperature for 1 hour. The mixture was poured into aqueous sodium bisulfite (10%, 500 mL) and extracted with ethyl acetate (2×500 mL). The combined organic fractions were washed with brine, dried (Na$_2$SO$_4$) and the solvent was evaporated under reduced pressure. The residue was triturated with hexane and the solid was collected and dried iii vacuo to give the title compound as a colourless solid (10.59 g, 49%). $^1$H NMR (400 MHz, CDCl$_3$) δ 7.82 (2H, s), 7.81 (1H, s), 5.57 (1H, m), 5.13 (1H, s), 5.10 (1H, m), 2.86 (1H, m), 2.73 (1H, m), and 1.69 (3H, s).

Description 11

(RS)-α-(3-Butenyl)-N-(4-oxo-1-phenylcyclohexyl)-3,5-bis(trifluoromethyl)-benzeneacetamide Oxalyl chloride (4.22 mL, 48.4 mmol) was added to a solution of (RS)-α-(3-butenyl)-3,5-bis(trifluoromethyl)benzeneacetic acid (Description 8, 24.2 mmol) and dimethylformamide (0.1 mL) in dichloromethane (80 mL) and the mixture was stirred at room temperature for 3 hours. The solvent was evaporated under reduced pressure and toluene was added and evaporated under reduced pressure. The residue was dissolved in dichloromethane (50 mL) and added to a stirred, cooled (0° C.) solution of 4-oxo-1-phenylcyclohexylamine hydrochloride (Description 3, 4.58 g, 24.2 mmol) in dichloromethane (150 mL). Pyridine (4.1 mL, 50.8 mmol) was added and the mixture was stirred at room temperature overnight. The mixture was washed with hydrochloric acid (1M, 2×200 mL), saturated aqueous sodium hydrogen carbonate (2×200 mL) and brine (200 mL), dried (MgSO$_4$) and the solvent was evaporated under reduced pressure. The residue was triturated with isohexane/diethylether (7:1) and the solid was collected and dried in vacuo. The solid was purified by flash column chromatography on silica gel, eluting with isohexane/EtOAc (2:1), to give the title compound (6.22 g, 52%). $^1$H NMR (400 MHz, CDCl$_3$) δ 7.80 (1H, s), 7.73 (2H, s), 7.31-7.25 (5H, m), 5.80-5.70 (2H, m), 5.05-4.97 (2H, m), 3.52-3.47 (1H, m), 2.86-2.80 (1H, m), 2.65-2.57 (1H, m), 2.50-2.31 (6H, m), 2.27-2.18 (1H, m), 2.09-1.95 (2H, m), and 1.81-1.72 (1H, m).

Description 12

(RS)-N-(4-Oxo-1-phenylcyclohexyl)-α-(2-propenyl)-3,5-bis(trifluoromethyl)-benzeneacetamide Prepared from (RS)-α-(2-propenyl)-3,5-bis(trifluoromethyl)benzeneacetic acid (Description 9) and 4-oxo-1-phenylcyclohexylamine hydrochloride (Description 3) according to the method of Description 11. $^1$H NMR (400 MHz, CDCl$_3$) δ 7.80 (1H, s), 7.73 (2H, s), 7.35-7.2 (5H, m), 5.80 (1H, br s), 5.75-5.63 (1H, m), 5.13-5.05 (2H, m), 3.56 (1H, dd, J 7, 6 Hz), 2.90-2.80 (21H, m), 2.65-2.55 (1H, m), and 2.52-2.30 (7H, m).

Description 13

(RS)-N-(4-Oxo-1-phenylcyclohexyl)-α-methyl-α-(2-propenyl)-3,5-bis(trifluoromethyl)benzeneacetamide Prepared from (RS)-α-methyl-α-(2-propenyl)-3,5-bis(trifluoromethyl)benzeneacetic acid (Description 10) and 4-oxo-1-phenylcyclohexylamine hydrochloride (Description 3) according to the method of Description 11. $^1$H NMR (360 MHz, CDCl$_3$) δ 7.81 (1H, s), 7.71 (2H, s), 7.35-7.27 (5H, m), 5.58 (1H, br s), 5.57-5.45 (1H, m), 5.09-5.03 (2H, m), 2.81-2.73 (2H, m), 2.66-2.60 (2H, m), 2.48-2.30 (6H, m), and 1.63 (3H, s).

Description 14

(RS)-α-(3-Butenyl)-N-(1,4-dioxa-8-phenylspiro[4.5]decan-8-yl)-3,5-bis(trifluoromethyl)benzeneacetamide Ethylene glycol (1.39 mL, 25 mmol) and p-toluenesulfonic acid (71 mg, 0.37 mmol) were added to a solution of (RS)-α-(3-butenyl)-N-(4-oxo-1-phenylcyclohexyl)-3,5-bis(trifluoromethyl)benzeneacetamide (Description 11, 6.22 g, 12.5 mmol) in toluene (200 mL) and the mixture was heated under reflux with azeotropic removal of water overnight. The mixture was cooled, potassium carbonate (13 g) was added and the mixture was stirred at room temperature for 10 minutes. Water (100 mL), aqueous sodium carbonate (10%, 100 mL) and ethyl acetate (200 mL) were added and the layers were separated. The aqueous layer was extracted with ethyl acetate (2×200 mL) and the combined organic fractions were washed with brine, dried (Na$_2$SO$_4$) and the solvent was evaporated under reduced pressure to give crude title compound (9.1 g) which was used without further purification. $^1$H NMR (400 MHz, CDCl$_3$) contains residual toluene δ 7.79 (1H, s), 7.73 (2H, s), 7.27-7.14 (5H, m), 5.79-5.72 (2H, m), 5.63 (1H, s), 5.05-4.99 (2H, m), 3.97-3.92 (4H, m), 3.49-3.45 (1H, m), 2.56-2.52 (1H, m), 2.25-2.12 (4H, m), 2.05-1.99 (2H, m), and 1.77-1.59 (5H, m).

Description 15

(RS)-N-(1,4-Dioxa-8-phenylspiro[4.5]decan-8-yl)-α-(2-propenyl)-3,5-bis(trifluoromethyl)benzeneacetamide Prepared from (RS)-N-(4-oxo-1-phenylcyclohexyl)-α-(2-propenyl)-3,5-bis(trifluoromethyl)benzeneacetamide (Description 12) according to the method of Description 14. $^1$H NMR (400 MHz, CDCl$_3$) δ 7.79 (1H, s), 7.73 (2H, s), 7.30-7.15 (5H, m), 5.75-5.60 (2H, m), 5.08 (1H, d, J 8 Hz), 5.04 (1H, s), 4.0-3.8 (4H, m), 3.52 (1H, t, J 7 h), 2.88-2.78 (1H, m), 2.58-2.48 (1H, m), 2.47-2.37 (1H, m), 2.26-2.06 (3H, m), and 1.75-1.55 (4H, m).

Description 16

(RS)-N-(1,4-Dioxa-8-phenylspiro[4.5]decan-8-yl)-α-methyl-α-(2-propenyl)-3,5-bis(trifluoromethyl)benzeneacetamide Prepared from (RS)-N-(4-oxo-1-phenylcyclohexyl)-α-methyl-α-(2-propenyl)-3,5-bis(trifluoromethyl)benzeneacetamide (Description 13) according to the method of Description 14. $^1$H NMR (400 MHz, CDCl$_3$) δ 7.81 (1H, s), 7.73 (2H, s), 7.30-7.19 (5H, m), 5.53-5.43 (2H, m), 5.08-5.02 (2H, m), 3.98-3.90 (4H, m), 2.80-2.74 (1H, m), 2.63-2.57 (1H, m), 2.48-2.43 (1H, m), 2.26-2.06 (3H, m), and 1.71-1.52 (7H, m).

Description 17

(RS)-α-(3-Hydroxypropyl)-N-(1,4-dioxa-8-phenylspiro[4.5]decan-8-yl)-3,5-bis(trifluoromethyl)benzeneacetamide Crude (RS)-α-(3-butenyl)-N-(1,4-dioxa-8-phenylspiro[4.5]decan-8-yl)-3,5-bis(trifluoromethyl)benzeneacetamide (Description 14, 9.1 g) was dissolved in methanol/dichloromethane (1:1, 120 mL) and cooled to −78° C. Oxygen was bubbled through the solution for 10 minutes, then ozone was bubbled through until the solution had gone from orange to grey/brown (about 50 minutes). The reaction was flushed with oxygen for 10 minutes, then with nitrogen for 10 minutes. Sodium borohydride (4.7 g, 125 mmol) was added and the mixture was stirred at −78° C. for 1 hour, then at room temperature overnight. Further portions of sodium borohydride (470 mg, 12.5 mmol) were added at 30 minutes intervals until effervescence ceased. Acetone (60 mL) was added and the mixture was stirred at room temperature for 10 minutes. Water (60 mL) was added and the solvent was evaporated under reduced pressure. Aqueous citric acid (10%, 150 mL) and ethyl acetate (150 mL) were added and the mixture was stirred for 30 minutes. The layers were separated and the aqueous layer was extracted with ethyl acetate (100 mL). The combined organic fractions were washed with water (2×100 mL) and brine (100 mL), dried (MgSO$_4$) and the solvent was evaporated under reduced pressure. The residue was purified by flash column chromatography on silica gel, eluting with EtOAc/isohexane (75:25), to give the title compound (5.38 g, 79% from (RS)-α-(3-butenyl)-N-(4-oxo-1-phenylcyclohexyl)-3,5-bis(trifluoromethyl)benzeneacetamide). $^1$H NMR (400 MHz, CDCl$_3$) δ 7.79 (1H, s), 7.74 (2H, s), 7.23-7.17 (5H, m), 5.83 (1H, s), 3.97-3.93 (4H, m), 3.70-3.56 (3H, m), 2.57-2.53 (1H, m), 2.26-2.08 (4H, m), and 1.77-1.52 (8H, m).

Description 18

(RS)-α-(2-Hydroxyethyl)-N-(1,4-dioxa-8-phenyl-spiro[4.5]decan-8-yl)-3,5-bis(trifluoromethyl)benzeneacetamide Prepared from (RS)-N-(1,4-dioxa-8-phenylspiro[4.5]decan-8-yl)-α-(2-propenyl)-3,5-bis(trifluoromethyl)benzeneacetamide (Description 15) according to the method of Description 17. $^1$H NMR (400 MHz, CDCl$_3$) δ 7.80 (1H, s), 7.78 (2H, s), 7.30-7.15 (5H, m), 5.93 (1H, br s), 4.0-3.9 (4H, m), 3.86 (1H, dd, J 9, 5.7 Hz), 3.70-3.50 (2H, m), 2.60-2.50 (1H, m), 2.39-2.28 (1H, m), 2.27-2.08 (3H, m), 2.00-1.83 (2H, m), and 1.78-1.60 (4H, m).

Description 19

(RS)-α-(2-Hydroxyethyl)-α-methyl-N-(,14-dioxa-8-phenylspiro[4.51]decan-8-yl)-3,5-bis(trifluoromethyl)benzeneacetamide Prepared from (RS)-N-(1,4-dioxa-8-phenylspiro[4.5]decan-8-yl)-α-methyl-α-(2-propenyl)-3,5-bis(trifluoromethyl)benzeneacetamide (Description 16) according to the method of Description 17. $^1$H NMR (400 MHz, CDCl$_3$) δ 7.82 (1H, s), 7.75 (2H, s), 7.31-7.20 (5H, m), 5.77 (1H, br s), 3.98-3.91 (4H, m), 3.69-3.62 (1H, m), 3.60-3.54 (1H, m), 2.50-2.45 (1H, m), 2.37-2.30 (1H, m), 2.24-2.17 (2H, m), 2.14-2.06 (2H, m), 1.99-1.89 (1H, m), and 1.75-1.53 (7H, m).

Description 20

(RS)-α-(3-Bromopropyl)-N-(1,4-dioxa-8-phenyl-spiro[4.5]decan-8-yl)-3,5-bis(trifluoromethyl)benzeneacetamide Triphenylphosphine (3.85 g, 14.66 mmol) in dichloromethane (50 mL) was added slowly to a stirred, cooled (0° C.) suspension of (RS)-α-(3-hydroxypropyl)-N-(1,4-dioxa-8-phenylspiro[4.5]decan-8-yl)-3,5-bis(trifluoromethyl)benzeneacetamide (Description 17, 3.2 g, 5.87 mmol) and carbon tetrabromide (4.86 g, 14.7 mmol) in dichloromethane (50 mL) and the mixture was stirred at 0° C. for 15 minutes then at room temperature for 1 hour. The solvent was evaporated under reduced pressure and the residue was purified by flash column chromatography on silica gel, eluting with isohexane/EtOAc (80:20), to give the title compound. $^1$H NMR (400 MHz, CDCl$_3$) δ 7.81 (1H, s), 7.73 (2H, s), 7.25-7.17 (5H, m), 5.65 (1H, s), 3.98-3.91 (4H, m), 3.49-3.31 (3H, m), 2.51-2.48 (1H, m), 2.26-2.09 (4H, m), and 1.91-1.56 (7H, m).

Description 21

(RS)-α-(2-Bromoethyl)-N-(1,4-dioxa-8-phenylspiro[4.5]decan-8-yl)-3,5-bis(trifluoromethyl)benzeneacetamide Prepared from (RS)-α-(2-hydroxyethyl)-N-(1,4-dioxa-8-phenylspiro[4.5]decan-8-yl)-3,5-bis(trifluoromethyl)benzeneacetamide (Description 18) according to the method of Description 20. m/z (ES$^+$) 594, 596 (M+1).

Description 22

1-(1,1-Dimethylethyl) 4-Ethyl 4-(2-Propenyl)-1,4-piperidinedicarboxylate

A solution of 1-(1,1-dimethylethyl) 4-ethyl 1,4-piperidinedicarboxylate (25.0 g, 97 mmol) in tetrahydrofuran (100 mL) was added slowly to a stirred, cooled (−78° C.) solution of potassium hexamethyldisilazide (29.0 g, 145 mmol) in tetrahydrofuran (150 mL), maintaining the internal temperature below −65° C. The mixture was stirred at −78° C. for 30 minutes, then 3-bromopropene (12.6 mL, 145 mmol) was added dropwise over 10 minutes. The mixture was stirred at −78° C. for 1 hour, then saturated aqueous ammonium chloride (400 mL) and water (100 mL) were added and the mixture was warmed to room temperature. The mixture was extracted with ethyl acetate (3×400 mL) and the combined organic fractions were washed with aqueous citric acid (10%, 2×250 mL), saturated aqueous sodium hydrogen carbonate (400 mL) and brine (200 mL), dried (MgSO$_4$) and the solvent was evaporated under reduced pressure to give the title compound (29.3 g, 100%). $^1$H NMR (400 MHz, CDCl$_3$) δ 5.75-5.60 (1H, m), 5.10-5.00 (2H, m), 4.16 (2H, q, J 7 Hz), 3.92-3.78 (2H, m), 2.90 (2H, br t, J 14 Hz), 2.26 (2H, d, J 7 Hz), 2.08 (2H, br d, J 14 Hz), 1.45 (9H, s), 1.45-1.30 (2H, m), and 1.26 (3H, t, J 7 Hz).

Description 23

1,1-Dimethylethyl 1-Oxo-2-oxa-8-azaspiro[4.5]decane-8-carboxylate 1-(1,1-Dimethylethyl) 4-ethyl 4-(2-propenyl)-1,4-piperidinedicarboxylate (Description 22, 20.0 g, 67.2 mmol) was dissolved in methanol (300 mL) and dichloromethane (300 mL) and cooled to −78° C. Oxygen was bubbled through the solution for 10 minutes, then ozone for 75 minutes, to give a persistent blue coloration. Oxygen was bubbled through the solution for 10 minutes, then nitrogen for 10 minutes. Sodium borohydride (5.1 g, 135 mmol) was added and the mixture was stirred at −78° C. for 1 hour. Further sodium borohydride (5.1 g, 135 mmol) was added and the mixture was stirred at room temperature for 16 hours. Acetone (75 mL) was added and the mixture was stirred at room temperature for 10 minutes. Water (50 mL) was added and the organic solvent was evaporated under reduced pressure. Saturated aqueous ammonium chloride (500 mL) was added and the mixture was extracted with ethyl acetate (2×500 mL). The combined organic fractions were washed with aqueous citric acid (10%, 500 mL), saturated aqueous sodium hydrogen carbonate (500 mL) and brine (200 mL), dried (Na$_2$SO$_4$) and the solvent was evaporated under reduced pressure to give the title compound (15.0 g, 88%). $^1$H NMR (400 MHz, CDCl$_3$) δ 4.31 (2H, t, J 7 Hz), 3.97-3.87 (2H, m), 3.17-3.07 (2H, m), 2.20 (2H, t, J 7 Hz), 1.92-1.82 (2H, m), 1.60-1.45 (2H, m), and 1.45 (9H, s).

Description 24

1,1-Dimethylethyl 4-(2-Hydroxyethyl)4-(hydroxymethyl)-1-piperidinecarboxylate

Diisobutylaluminium hydride (1.0M in dichloromethane, 3.60 mL, 3.60 mmol) was added over 10 minutes to a stirred, cooled (−78° C.) solution of 1,1-dimethylethyl 1-oxo-2-oxa-8-azaspiro[4.5]decane-8-carboxylate (Description 23, 400 mg, 1.57 mmol) in dichloromethane (4 mL) and the mixture stirred at −78° C. for 3 hours, then at 0° C. for 2 hours. Water (1.6 mL) was added very slowly at 0° C. and the mixture was warmed to room temperature and stirred overnight. The mixture was filtered through Hyflo™, washing with dichloromethane, and the solvent was evaporated under reduced pressure. The residue was purified by flash column chromatography on silica gel, eluting with ethyl acetate, to give the title compound (255 mg, 63%). m/z (ES$^+$) 260 (M+1).

Description 25

1,1-Dimethylethyl 2-Oxa-8-azaspiro[4.5]decane-8-carboxylate

Diethyl azodicarboxylate (183 μl, 1.16 mmol) in tetrahydrofuran (0.5 mL) was added dropwise to a stirred, cooled (0° C.) solution of 1,1-dimethylethyl 4-(2-hydroxyethyl)-4-(hydroxymethyl)-1-piperidinecarboxylate Description 24, 250 mg, 0.96 mmol) and triphenylphosphine (303 mg, 1.16 mmol) in tetrahydrofuran (10 mL) and the mixture was stirred at 0° C. for 90 minutes then at room temperature overnight. The mixture was cooled to 0° C. and further triphenylphosphine (126 mg, 0.48 mmol) and diethyl azodicarboxylate (76 μl, 0.48 mmol) were added. The mixture was stirred at room temperature for 2.5 hours, then the solvent was evaporated under reduced pressure and the residue was purified by flash column chromatography on silica gel, eluting with isohexane/EtOAc (80:20), to give the title compound as a colorless oil (150 mg, 65%). m/z (ES$^+$) 186 (M+1−C$_4$H$_8$).

Description 26

2-Oxa-8-azaspiro[4.5]decane

Methanolic hydrogen chloride (3M, 3 mL) was added to a stirred, cooled (0° C.) solution of 1,1-dimethylethyl 2-oxa-8-azaspiro[4.5]decane-8-carboxylate (Description 25, 150 mg, 0.62 mmol) in methanol and the mixture was stirred at room temperature for 24 hours. The solvent was evaporated under reduced pressure and the residue was dissolved in methanol and passed through Amberlyst™ 26 ion exchange resin, eluting with methanol. The solvent was evaporated under reduced pressure and the residue was dissolved in dichloromethane, dried (Na$_2$SO$_4$) and the solvent was evaporated under reduced pressure to give the title compound (77 mg, 88%). m/z (ES$^+$) 142 (M+1).

EXAMPLE 1

(RS)-3-[3,5-Bis(trifluoromethyl)phenyl]-1-(1,4-dioxa-8-phenylspiro[4.5]decan-8-yl)-2-piperidinone Sodium hexamethyldisilazide (1.0M in tetrahydrofuran, 1.64 mL, 1.64 mmol) was added dropwise under argon to a stirred, cooled (−78° C.), rigourously degassed solution of (RS)-α-(3-bromopropyl)-N-(1,4-dioxa-8-phenylspiro[4.5]decan-8-yl)-3,5-bis(trifluoromethyl)benzeneacetamide (Description 20, 1.0 g, 1.64 mmol) in tetrahydrofuran (20 mL) and the mixture was stirred at −78° C. for 5 minutes, then at room temperature for 30 minutes. The mixture was cooled to −78° C. and further sodium hexamethyldisilazide (1.0M in tetrahydrofuran, 0.5 mL, 0.5 mmol) was added. The mixture was stirred at room temperature for 30 minutes, then saturated aqueous ammonium chloride (10 mL) and water (20 mL) were added. The mixture was extracted with ethyl acetate (2×20 mL), and the combined organic fractions were washed with brine, dried (MgSO$_4$) and the solvent was evaporated under reduced pressure. The residue was purified by flash column chromatography on silica gel, eluting with isohexane/EtOAc (67:33). The residue was purified by MPLC on silica gel, eluting with isohexane/EtOAc (67:33), to give the title compound (510 mg, 59%). $^1$H NMR (400 MHz, CDCl$_3$) δ 7.73 (1H, s), 7.62 (2H, s), 7.50 (2H, dd, J 1.0, 8.4 Hz), 7.35-7.31 (2H, m), 7.27-7.22 (1H, m), 4.00-3.93 (4H, m), 3.79 (1H, dd, J 6.8, 10.0 Hz), 3.45 (1H, d, J 4.7 Hz), 3.45-3.42 (1H, m), 2.91-2.88 (1H, m), 2.79-2.75 (1H, m), 2.34-2.16 (3H, m), and 1.95-1.63 (7H, m).

EXAMPLE 2

(RS)-3-[3,5-Bis(trifluoromethyl)phenyl]-1-(1,4-dioxa-8-phenylspiro[4.5]decan-8-yl)-2-pyrrolidinone Sodium hydride (60% dispersion in mineral oil, 40 mg, 1.00 mmol) was added to a rigourously degassed solution of (RS)-α-(2-bromoethyl)-N-(1,4-dioxa-8-phenylspiro[4.5]decan-8-yl)-3,5-bis(trifluoromethyl)benzeneacetamide (Description 21, 600 mg, 1.01 mmol) in tetrahydrofuran (15 mL) and the mixture was stirred at room temperature for 1 hour. Further sodium hydride (60% dispersion in mineral oil, 40 mg, 1.00 mmol) was added and the mixture was stirred at room temperature for 20 minutes. Saturated ammonium chloride (5 mL) and water (10 mL) were added and the mixture was extracted with ethyl acetate (2×20 mL). The combined organic fractions were washed with brine (20 mL), dried (Na$_2$SO$_4$) and the solvent was evaporated under reduced pressure. The residue was triturated with isohexane (2×5 mL) and the solid was collected and dried in vacuo to give the title compound (455 mg, 88%). $^1$H NMR (400 MHz, CDCl$_3$) δ 7.78 (1H, s), 7.70 (2H, s), 7.47 (2H, d, J 7 Hz), 7.34 (2H, t, J 7 Hz), 7.30-7.25 (1H, m), 4.02-3.92 (4H, m), 3.80 (1H, t, J 9.5 Hz), 3.39 (2H, m), 2.93 (1H, br d, J 13 Hz), 2.80 (1H, br d, J 13 Hz), 2.52-2.42 (1H, m), 2.33-2.23 (1H, m), 2.22-2.12 (1H, m), 2.12-2.01 (1H, m), and 1.90-1.70 (4H, m). m/z (ES$^+$) 514 (M+1).

EXAMPLE 3

(RS)-3-Hydroxy-3-[3,5-bis(trifluoromethyl)phenyl]-1-(1,4-dioxa-8-phenylspiro[4.5]decan-8-yl)-2-pyrrolidinone Sodium hydride (60% dispersion in mineral oil, 150 mg, 3.75 mmol) was added to a solution of (RS)-α-(2-bromoethyl)-N-(1,4-dioxa-8-phenylspiro[4.5]decan-8-yl)-3,5-bis(trifluoromethyl)benzeneacetamide (Description 21, 430 mg, 0.723 mmol) in tetrahydrofuran (5 mL) and the mixture was stirred at room temperature for 20 hours. Aqueous citric acid (10%, 20 mL) was added and the mixture was extracted with ethyl acetate (2×20 mL). The combined organic fractions were washed with water (20 mL), dried ($Na_2SO_4$) and the solvent was evaporated under reduced pressure. The residue was purified by flash column chromatography on silica gel, eluting with isohexane/EtOAc (75:25 increasing to 50:50), to give the title compound (142 mg, 38%). $^1$H NMR (400 MHz, $CDCl_3$) δ 7.85 (3H, s), 7.48 (2H, d, J 7 Hz), 7.37 (2H, t, J 7 Hz), 7.30 (1H, t, J 7 Hz), 4.02-3.90 (4H, m), 3.40 (1H, dt, J 8, 3 Hz), 3.23 (1H, q, J 8 Hz), 2.98 (1H, br d, J 13 Hz), 2.72 (1H, br d, J 13 Hz), 2.48-2.18 (4H, m), 1.85-1.65 (4H, m), and 1.6 (1H, br s).

EXAMPLE 4

(RS)-3-Methyl-3-[3,5-bis(trifluoromethyl)phenyl]-1-(1,4-dioxa-8-phenylspiro[4.5]decan-8-yl)-2-pyrrolidinone Sodium hexamethyldisilazide (1M in tetrahydrofuran, 8.8 mL, 8.8 mmol) was added dropwise to a stirred, cooled (−78° C.) solution of (RS)-α-(2-hydroxyethyl)-α-methyl-N-(1,4-dioxa-8-phenylspiro[4.5]decan-8-yl)-3,5-bis(trifluoromethyl)benzeneacetamide (Description 19, 2.09 g, 3.83 mmol) in tetrahydrofuran (100 mL) and the mixture was stirred at −78° C. for 30 minutes. Methanesulfonyl chloride (0.44 mL, 0.66 g, 5.8 mmol) was added and the mixture was stirred at −78° C. for 10 minutes, then allowed to warm to room temperature. Saturated aqueous ammonium chloride (100 mL) and water (20 mL) were added and the mixture was extracted with ethyl acetate (2×100 mL). The combined organic fractions were dried ($Na_2SO_4$) and the solvent was evaporated under reduced pressure. The residue was purified by flash column chromatography on silica gel, eluting with isohexane/EtOAc (75:25 increasing to 70:30), to give the title compound (340 mg, 17%). $^1$H NMR (400 MHz, $CDCl_3$) δ 7.85 (2H, s), 7.75 (1H, s), 7.45-7.23 (5H, m), 3.95 (4H, m), 3.28 (1H, m), 3.20 (1H, m), 2.86 (2H, m), 2.36 (1H, m), 2.23 (2H, m), 2.11 (1H, m), 1.72 (4H, m), and 1.51 (3H, s).

EXAMPLE 5

(RS)-3-[3,5-Bis(trifluoromethyl)phenyl]-1-(4-oxo-1-phenylcyclohexyl)-2-piperidinone Hydrochloric acid (2M, 15 mL) was added to a solution of (RS)-3-[3,5-bis(trifluoromethyl)phenyl]-1-(1,4-dioxa-8-phenylspiro[4.5]decan-8-yl)-2-piperidinone (Example 1, 210 mg, 0.59 mmol) in acetone (15 mL) and the mixture was heated at 50° C. for 5 hours. The mixture was cooled, neutralised with aqueous sodium carbonate (10%) and extracted with ethyl acetate (75 mL). The organic fraction was washed with brine, dried ($MgSO_4$) and the solvent was evaporated under reduced pressure to give the title compound (275 mg, 96%). $^1$H NMR (400 MHz, $CDCl_3$) δ 7.76 (1H, s), 7.63 (2H, s), 7.52-7.49 (2H, m), 7.41-7.37 (2H, m), 7.33-7.29 (1H, m), 3.83 (1H, dd, J 6.8, 10.0 Hz), 3.43 (2H, t, J 5.9 Hz), 3.18-3.13 (1H, m), 3.09-3.04 (1H, m), 2.63-2.55 (1H, m), 2.52-2.33 (5H, m), 2.25-2.21 (1H, m), and 1.97-1.81 (3H, m).

EXAMPLE 6

(RS)-3-[3,5-Bis(trifluoromethyl)phenyl]-1-(4-oxo-1-phenylcyclohexyl)-2-pyrrolidinone Prepared from (RS)-3-[3,5-Bis(trifluoromethyl)phenyl]-1-(1,4-dioxa-8-phenylspiro[4.5]decan-8-yl)-2-pyrrolidinone (Example 2) according to the method of Example 5. $^1$H NMR (400 MHz, $CDCl_3$) δ 7.80 (1H, s), 7.71 (2H, s), 7.52-7.28 (5H, m), 3.85 (1H, t, J 9.5 Hz), 3.42-3.38 (2H, m), 3.23-3.07 (2H, m), 2.70-2.30 (7H, m), and 2.18-2.05 (1H, m). m/z ($ES^+$) 470 (M+1).

EXAMPLE 7

(RS)-3-Hydroxy-3-[3,5-bis(trifluoromethyl)phenyl]-1-(4-oxo-1-phenylcyclohexyl)-2-pyrrolidinone Prepared from (RS)-3-hydroxy-3-[3,5-bis(trifluoromethyl)phenyl]-1-(1,4-dioxa-8-phenylspiro[4.5]decan-8-yl)-2-pyrrolidinone (Example 3) according to the method of Example 5. $^1$H NMR (400 MHz, $CDCl_3$) δ 7.82 (1H, s), 7.80 (2H, s), 7.53-7.33 (5H, m), 3.45-3.38 (1H, m), 3.29-3.19 (2H, m), 3.10-3.00 (1H, m), and 2.60-2.30 (8H, m).

EXAMPLE 8

(RS)-3-Methyl-3-[3,5-bis(trifluoromethyl)phenyl]-1-(1,4-dioxa-8-phenylspiro[4.5]decan-8-yl)-2-pyrrolidinone Prepared from (RS)-3-methyl-3-[3,5-bis(trifluoromethyl)phenyl]-1-(1,4-dioxa-8-phenylspiro[4.5]decan-8-yl)-2-pyrrolidinone (Example 4) according to the method of Example 5. $^1$H NMR (360 MHz, $CDCl_3$) δ 7.86 (2H, s), 7.77 (1H, s), 7.46-7.29 (5H, m), 3.22 (3H, m), 3.07 (1H, m), 2.58-2.28 (7H, m), 2.15 (1H, m), and 1.54 (3H, s).

EXAMPLE 9

Cis-(RS)-3-[3,5-Bis(trifluoromethyl)phenyl]-1-[4-(2-oxa-8-azaspiro[4.5]decan-8-yl)-1-phenylcyclohexyl]-2-piperidinone and Trans-(RS)-3-[3,5-Bis(trifluoromethyl)phenyl]-1-[4-(2-oxa-8-azaspiro[4.5]decan-8-yl)-1-phenylcyclohexyl]-2-piperidinone Triethylamine (56 μl, 0.40 mmol) was added to a suspension of 2-oxa-8-azaspiro[4.5]decane hydrochloride (Description 26, 55 mg, 0.31 mmol) in 1,2-dichloroethane (10 mL) and the mixture was sonicated until the solid dissolved. (RS)-3-[3,5-Bis(trifluoromethyl)phenyl]-1-(4-oxo-1-phenylcyclohexyl)-2-piperidinone (Example 5, 100 mg, 0.21 mmol) and sodium triacetoxyborohydride (49 mg, 0.23 mmol) were added and the mixture was stirred at room temperature overnight. Further portions of sodium triacetoxyborohydride (22 mg, 0.1 mmol) were added at 4 hour intervals until the reaction was complete (monitoring by HPLC). The mixture was poured into saturated aqueous sodium hydrogen carbonate (30 mL) and extracted with dichloromethane (30 mL). The organic fraction was washed with brine, dried ($Na_2SO_4$) and the solvent was evaporated under reduced pressure. The residue was dissolved in methanol (1.5 mL) and poured onto an SCX cartridge (Varian Bond Elut™; 10 ml/500 mg). The cartridge was washed with methanol (4×2 mL), then eluted with methanolic ammonia (2M, 2×2 mL). The solvent was evaporated under reduced pressure and the residue was purified by MPLC on silica gel, eluting with CH₂Cl₂/MeOH/NH₃(Aq.) (96:4:0.4) to give cis-(RS)-3-[3,5-bis(trifluoromethyl)phenyl]-1-[4-(2-oxa-8-azaspiro[4.5]decan-8-yl)-1-phenylcyclohexyl]-2-piperidinone; ¹H NMR (400 Hz, CD₃OD) δ 7.86 (3H, s), 7.47 (2H, d, J 7.4 Hz), 7.36 (2H, t, J 7.4 Hz), 7.25 (1H, t, J 7.4 Hz), 4.05 (1H, dd, J 10.7, 6.9 Hz), 3.90 (2H, t, J 7.1 Hz), 3.60-3.05 (11H, m), 2.23 (1H, m), 2.13-2.00 (3H, m), and 1.90-1.64 (12H, m); m/z (ES⁺) 608 (M+1); and trans-(RS)-3-[3,5-bis(trifluoromethyl)phenyl]-1-[4-(2-oxa-8-azaspiro[4.5]decan-8-yl)-1-phenylcyclohexyl]-2-piperidinone; ¹H NMR (400 MHz, CD₃OD) δ 7.76 (1H, s), 7.63 (2H, d, J 7.5 Hz), 7.57 (2H, s), 7.37 (2H, t, J 7.5 Hz), 7.26 (1H, t, J 7.5 Hz), 3.86 (2H, m), 3.76 (1H, dd, J 9.6, 6.7 Hz), 3.66 (2H, t, J 5.5 Hz), 3.51-3.30 (6H, m), 3.15 (1H, m), 3.02 (2H, br m), 2.37-2.08 (5H, m), 1.94-1.79 (9H, m), 1.63 (1H, m), and 1.45 (1H, m); m/z (ES⁺) 608 (M+1).

The following compounds were prepared from (RS)-3-[3,5-bis(trifluoromethyl)phenyl]-1-(4-oxo-1-phenylcyclohexyl)-2-piperidinone (Example 5), (RS)-3-[3,5-bis(trifluoromethyl)phenyl]-1-(4-oxo-1-phenylcyclohexyl)-2-pyrrolidinone (Example 6), (RS)-3-hydroxy-3-[3,5-bis(trifluoromethyl)phenyl]-1-(4-oxo-1-phenylcyclohexyl)-2-pyrrolidinone (Example 7) or (RS)-3-methyl-[3,5-bis(trifluoromethyl)phenyl]-1-(4-oxo-1-phenylcyclohexyl)-2-pyrrolidinone (Example 8), according to the method of Example 9, substituting a suitable amine for 2-oxa-8-azaspiro[4.5]decane.

| Ex. | n | X | —NR₂ | Stereochemistry | Formula | M.W. | m/z (ES⁺) (M + 1) |
|---|---|---|---|---|---|---|---|
| 10[1] | 2 | H | piperazinone-N-Ph | Cis-(RS)- | $C_{35}H_{35}F_6N_3O_2$ | 643 | 644 |
| 11[1] | 2 | H | piperazinone-N-Ph | Trans-(RS)- | $C_{35}H_{36}N_3O_2F_6$ | 643 | 644 |
| 12 | 1 | H | 2-oxa-8-azaspiro[4.5]decane | Cis-(RS)- | $C_{32}H_{36}F_6N_2O_2$ | 594 | 595 |
| 13 | 1 | H | 2-oxa-8-azaspiro[4.5]decane | Trans-(RS)- | $C_{32}H_{36}F_6N_2O_2$ | 594 | 595 |
| 14[1] | 1 | H | piperazinone-N-Ph | Cis-(RS)- | $C_{34}H_{33}F_6N_3O_2$ | 629 | 630 |
| 15[1] | 1 | H | piperazinone-N-Ph | Trans-(RS)- | $C_{34}H_{33}F_6N_3O_2$ | 629 | 630 |
| 16 | 1 | OH | 2-oxa-8-azaspiro[4.5]decane | Cis-(RS)- | $C_{32}H_{36}F_6N_2O_3$ | 610 | 611 |

-continued

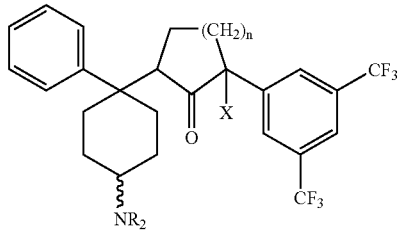

| Ex. | n | X | —NR₂ | Stereochemistry | Formula | M.W. | m/z (ES⁺) (M + 1) |
|---|---|---|---|---|---|---|---|
| 17 | 1 | OH | piperidine-spiro-tetrahydrofuran | Trans-(RS)- | $C_{32}H_{36}F_6N_2O_3$ | 610 | 611 |
| 18 | 1 | Me | piperidine-spiro-tetrahydrofuran | Cis-(RS)- | $C_{33}H_{38}F_6N_2O_2$ | 608 | 609 |
| 19 | 1 | Me | piperidine-spiro-tetrahydrofuran | Trans-(RS)- | $C_{33}H_{38}F_6N_2O_2$ | 608 | 609 |
| 20[1] | 1 | Me | 4-phenyl-piperazin-2-one | Trans-(RS)- | $C_{35}H_{36}N_3O_2F_6$ | 643 | 644 |
| 21[1] | 1 | Me | 4-phenyl-piperazin-2-one | Cis-(RS)- | $C_{35}H_{36}N_3O_2F_6$ | 643 | 644 |

[1]1-Phenyl-piperazinone: Tetrahedron Lett. 1998, 39, 7459–7462.

EXAMPLE 22

Trans-(RS)-3-[3,5-Bis(trifluoromethyl)phenyl]-1-(4-dimethylamino-1-phenylcyclohexyl)-2-pyrrolidinone A solution of zinc chloride (87 mg, 0.064 mmol) and sodium cyanoborohydride (80 mg, 0.13 mmol) in methanol (2 mL) was added to a solution of (RS)-3-[3,5-bis(trifluoromethyl)phenyl]-1-(4-oxo-1-phenylcyclohexyl)-2-pyrrolidinone (Example 6, 50 g, 0.11 mmol) and methanolic dimethylamine (2M, 0.16 mL, 0.32 mmol) in methanol (5 mL) and the mixture was stirred at room temperature for 24 hours. The solvent was evaporated under reduced pressure and water (10 mL) was added. The mixture was extracted with ethyl acetate (2×10 mL) and the combined organic fractions were dried (Na₂SO₄) and the solvent was evaporated under reduced pressure. The residue was purified by flash column chromatography on silica gel, eluting with CH₂Cl₂/MeOH/NH₃(Aq.) (95:5:0.5), then by preparative HPLC (Hichrom RPB 250×21.0 mm i.d.; 0.1% TFA-H₂O/ 43% MeCN; 20 mL/min; 210 nm; 100 µl injections of a 29 mg/mL solution in MeOH) to give the title compound (2.3 mg, 4%). ¹H NMR (400 MHz, CDCl₃) δ 7.75 (1H, s), 7.62 (2H, s), 7.54 (2H, d, J 7 Hz), 7.38 (2H, t, J 7 Hz), 7.29 (1H, t, J 7 Hz), 3.67 (1H, t, J 9.2 Hz), 3.40-3.27 (2H, m), 2.93 (1H, br d, J 13 Hz), 2.84 (1H, br d, J 13 Hz), 2.43-2.23 (4H, m), 2.21 (6H, s), 2.03-1.92 (1H, m), 1.89-1.79 (2H, m), and 1.50-1.33 (2H, m). m/z (ES⁺) 500 (M+1).

EXAMPLE 23

Trans-(RS)-3-Hydroxy-3-[3,5-bis(trifluoromethyl) phenyl]-1-[4-(2-oxa-8-azaspiro[4.5]decan-8-yl)-1-phenylcyclohexyl]-2-piperidinone, Trans-(RS)-3-Methoxy-3-[3,5-bis(trifluoromethyl)phenyl]-1-[4-(2-oxa-8-azaspiro[4.5]decan-8-yl)-1-phenylcyclohexyl]-2-piperidinone, and Trans-(RS)-3-Methyl-3-[3,5-bis(trifluoromethyl)phenyl]-1-[4-(2-oxa-8-azaspiro[4.5]decan-8-yl)-1-phenylcyclohexyl]-2-piperidinone Sodium hydride (60% dispersion in mineral oil; 3 mg, 0.077 mmol) was added to a solution of traits-(RS)-3-[3,5-bis(trifluoromethyl)phenyl]-1-[4-(2-oxa-8-azaspiro[4.5]decan-8-yl)-1-phenylcyclohexyl]-2-piperidinone (Example 13, 46 mg, 0.077 mmol) in dimethylformamide (2 mL) and the mixture was stirred at room temperature for 10 minutes. Methyl iodide (4.8 µl, 0.077 mmol) was added and the mixture was stirred at room temperature for 15 minutes. Water (25 mL) was added and the mixture was extracted with ethyl acetate (2×25 mL). The combined organic fractions were washed with water (2×25 mL) and brine, dried (Na₂SO₄) and the solvent was evaporated under reduced pressure. The residue was purified by flash column chromatography on silica gel, eluting with $CH_2Cl_2/MeOH/NH_3$ (Aq.) (95:5:0.5) to give trans-(RS)-3-[3,5-bis(trifluoromethyl)phenyl]-3-hydroxy-1-[4-(2-oxa-8-azaspiro[4.5]decan-8-yl)-1-phenylcyclohexyl]-2-piperidinone (10 mg, 21%); $^1H$ NMR (360 MHz, $CDCl_3$) δ 7.77 (1H, s), 7.70 (2H, s), 7.54 (2H, dd, J 1.3, 8.7 Hz), 7.40 (2H, t, J 7.5 Hz), 7.32 (1H, t, J 7.25 Hz), 3.81 (2H, t, J 7 Hz), 3.49 (2H, s), 3.37-3.31 (1H, m), 3.13-3.03 (2H, m), 2.92 (1H, d, J 13 Hz), 2.58-2.45 (5H, m), 2.41-2.26 (3H, m), 2.22-2.16 (1H, m), 1.94-1.88 (2H, m), 1.68 (2H, t, J7 Hz), 1.65-1.58 (4H, m), and 1.47 (2H, q, J 10.5 Hz); m/z ($ES^+$) 611 (M+1).

Mixed fractions were collected and purified by preparative HPLC (ABZ+plus 250×21.0 mm i.d.; 0.1% $TFA-H_2O$/ 45% MeCN; 20 mL/min; 210 nm; 75 μl injections of a 45 mg/mL solution in MeOH) to give trans-(RS)-3-[3,5-bis (trifluorozetliyl)phenyl]-3-methoxy-1-[4-(2-oxa-8-azaspiro [4.5]decan-8-yl)-1-phenylcyclohexyl]-2-piperidinone (13 mg, 26%); $^1H$ NMR (400 MHz, $CDCl_3$) δ 7.79 (1H, s), 7.77 (2H, s), 7.56-7.53 (2H, m), 7.38-7.34 (2H, m), 7.29-7.26 (1H, m), 3.81 (2H, t, J7 Hz), 3.49 (2H, s), 3.44-3.40 (1H, m), 3.16-3.13 (1H, m), 3.12 (3H, s), 3.03-2.89 (2H, m), 2.42-2.27 (8H, m), 2.08-2.02 (1H, m), 1.86-1.83 (2H, m), 1.69-1.65 (2H, m), 1.57-1.55 (4H, m), and 1.48-1.35 (2H, m); m/z ($ES^+$) 625 (M+1); and trans-(RS)-3-[3,5-bis(trifluoromethyl)phenyl]-3-methyl-]-[4-(2-oxa-8-azaspiro[4.5]decan-8-yl)-1-phenylcyclohexyl]-2-piperidinone (7 mg, 14%). $^1H$ NMR (400 MHz, $CDCl_3$) δ 7.73 (2H, s), 7.72 (1H, s), 7.52-7.50 (2H, m), 7.36-7.32 (2H, m), 7.28-7.24 (1H, m), 3.80 (2H, t, J 7 Hz), 3.48 (2H, s), 3.25-3.20 (1H, m), 3.15-3.09 (1H, m), 2.97-2.92 (2H, m), 2.47-2.21 (8H, m), 2.06-1.99 (1H, m), 1.86-1.78 (2H, m), 1.68-1.52 (6H, m), 1.56-1.36 (2H, m), and 1.40 (3H, s); m/z ($ES^+$) 609 (M+1).

The invention claimed is:

1. A compound of the formula (I):

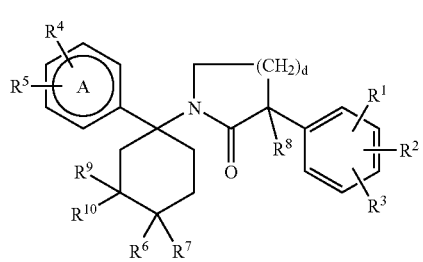

wherein:
ring A is a phenyl or pyridyl ring;

$R^1$ represents hydroxy, $C_{1-6}$alkyl, fluoro$C_{1-6}$alkyl, $C_{2-6}$alkenyl, $C_{3-7}$cycloalkyl, $C_{3-7}$cycloalkyl$C_{1-4}$alkyl, $C_{1-6}$alkoxy, fluoro$C_{1-6}$alkoxy, $C_{1-6}$alkoxy$C_{1-6}$alkyl, $C_{1-6}$alkoxy$C_{1-4}$alkoxy, fluoro$C_{1-6}$alkoxy$C_{1-4}$alkyl, $C_{2-6}$alkenyloxy, $C_{3-7}$cycloalkoxy, $C_{3-7}$cycloalkyl$C_{1-4}$alkoxy, phenoxy, cyano, halogen, $NR^aR^b$, $SR^a$, $SOR^a$, $SO_2R^a$, $OSO_2R^a$, $NR^aCOR^c$, $COR^a$, $CO_2R^a$ or $CONR^aR^b$ where $R^a$ and $R^b$ each independently represent hydrogen, $C_{1-4}$alkyl, $C_{3-5}$cycloalkyl, fluoro$C_{1-4}$alkyl or $CH_2CO_2C_{1-4}$alkyl, and $R^c$ represents $C_{1-6}$alkyl, $C_{1-6}$alkoxy, fluoro$C_{1-6}$alkyl or phenyl;

$R^2$ represents hydrogen, halogen, $C_{1-6}$alkyl or $C_{1-6}$alkoxy; or when $R^2$ is adjacent to $R^1$, they may be joined together such that there is formed a 5- or 6-membered saturated or unsaturated ring containing one or two atoms selected from nitrogen, oxygen and sulphur, which ring is optionally substituted by a group selected from $C_{1-4}$alkyl, $CF_3$, =O or =S;

$R^3$ represents hydrogen, halogen, $C_{1-6}$alkyl, fluoro$C_{1-6}$alkyl, $C_{1-6}$alkoxy, fluoro$C_{1-6}$alkoxy, $C_{3-7}$cycloalkyl, $C_{3-7}$cycloalkyl$C_{1-4}$alkyl, cyano, $SR^a$, $SOR^a$, $SO_2R^a$, $NR^aR^b$, $NR^aCOR^c$, $COR^a$, $CO_2R^a$, $CONR^aR^b$ or $C_{1-4}$alkyl substituted by cyano, $CO_2R^a$ or $CONR^aR^b$ where $R^a$, $R^b$ and $R^c$ are as previously defined;

or $R^3$ represents a 5- or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalkyl, $C_{3-7}$cycloalkyl$C_{1-4}$alkyl, trifluoromethyl, $OCF_3$, $NO_2$, CN, $SR^a$, $SOR^a$, $SO_2R^a$, $COR^a$, $CO_2R^a$, phenyl, $—(CH_2)_r NR^aR^b$, $—(CH_2)_rNR^aCOR^b$, $—(CH_2)_rCONR^aR^b$, or $CH_2C(O)R^a$, where $R^a$ and $R^b$ are as previously defined and r is zero, 1 or 2;

$R^4$ represents hydrogen, halogen, $C_{1-6}$alkyl, $C_{1-6}$alkoxy, fluoro$C_{1-6}$alkyl, fluoro$C_{1-6}$alkoxy, hydroxy, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

$R^5$ represents hydrogen, halogen, $C_{1-6}$alkyl, fluoro$C_{1-6}$alkyl or $C_{1-6}$alkoxy substituted by $C_{1-4}$alkoxy;

$R^6$ represents hydrogen, hydroxy or a $C_{1-4}$alkyl group optionally substituted by a hydroxy group;

$R^7$ represents hydrogen, hydroxy, $—(CH_2)_nNR^{11}R^{12}$, $—(CH_2)_nCO_2R^a$, carbocyclyl, C-linked heterocyclyl or heteroaryl, where $R^a$ is as previously defined;

or $R^6$ and $R^7$ together represent =O, =$CHCO_2R^a$ or $—O(CH_2)_mO—$, where $R^a$ is as previously defined;

$R^8$ represents hydrogen, hydroxy, $C_{1-6}$alkyl, $C_{1-6}$alkoxy, hydroxy$C_{1-6}$alkyl, $C_{2-6}$alkenyl, $C_{2-6}$alkynyl, $C_{1-4}$alkyl substituted by $C_{1-4}$alkoxy or $C_{1-6}$alkoxy substituted by $C_{1-4}$alkoxy;

$R^9$ represents hydrogen, halogen or hydroxy and $R^{10}$ represents hydrogen;

or $R^9$ and $R^{10}$ both represent fluorine or together represent oxo (=O);

$R^{11}$ and $R^{12}$ each independently represent hydrogen, $C_{1-6}$alkyl, $C_{2-6}$alkenyl, hydroxy$C_{1-6}$alkyl, $(CH_2)_qC_{3-7}$cycloalkyl, $(CH_2)_q$aryl, $(CH_2)_q$heterocyclyl, CHO, $C(O)C_{1-6}$alkyl, $C(O)(CH_2)_qC_{3-7}$cycloalkyl, $C(O)(CH_2)_q$ aryl, $C(O)(CH_2)_q$heterocyclyl, $C(O)(CH_2)_pN-R^aR^b$, $(CH_2)_qCO_2C_{1-6}$alkyl, $CO_2(CH_2)_qC_{3-7}$cycloalkyl, $CO_2(CH_2)_q$aryl, $CO_2(CH_2)_q$heterocyclyl, $CO_2(CH_2)_pNR^aR^b$, $(CH_2)_pNR^aCOR^b$, $(CH_2)_p NR^aCO_2R^b$, $(CH_2)_qCONR^a$aryl or $(CH_2)_qCONR^a$heterocyclyl where $R^a$ and $R^b$ are as previously defined;

or $R^{11}$ and $R^{12}$, together with the nitrogen atom to which they are attached, represent a ring selected from the group consisting of:

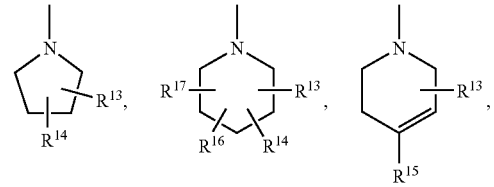

-continued

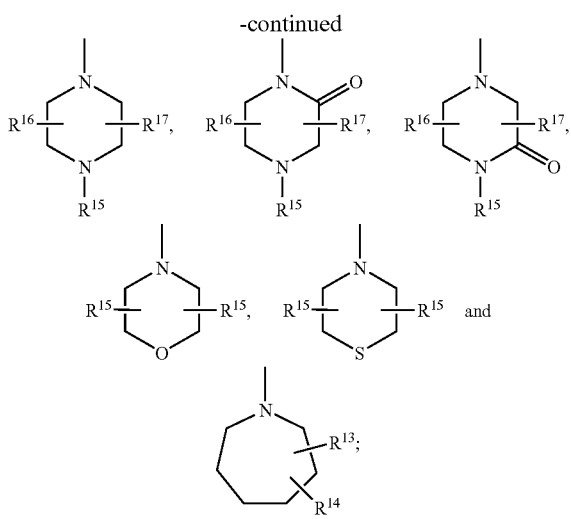

$R^{13}$ and $R^{14}$ each independently represent hydrogen, halogen, hydroxy, $C_{1-6}$alkyl, $C_{2-6}$alkenyl, $C_{2-6}$alkynyl, hydroxy$C_{1-6}$alkyl, fluoro$C_{1-6}$alkyl, $C_{1-6}$alkoxy, $(CH_2)_q C_{3-7}$cycloalkyl, $(CH_2)_q$aryl, $(C_{2-6}$alkenyl)aryl, $(C_{2-6}$alkynyl)aryl, $(CH_2)_q$heterocyclyl, $(CH_2)_q NR^a R^b$, $O(CH_2)_q C_{3-7}$cycloalkyl, $O(CH_2)_q$aryl, $O(CH_2)_q$heterocyclyl, $O(CH_2)_p NR^a R^b$, $OC(O)C_{1-6}$alkyl, $C(O)C_{1-6}$alkyl, $C(O)(CH_2)_q$aryl, $C(O)(CH_2)_q$heterocyclyl, $C(O)(CH_2)_q NR^a R^b$, $CO_2H$, $CO_2 C_{1-6alkyl}$, $CO_2(CH_2)_q C_{3-7}$cycloalkyl, $CO_2(CH_2)_q$aryl, $CO_2(CH_2)_q$heterocyclyl or $CO_2(CH_2)_p NR^a R^b$, where $R^a$ and $R^a$ are as previously defined;

or, when they are attached to the same carbon atom, $R^{13}$ and $R^{14}$ may together represent =O, =CHCO$_2$R$^a$, —O(CH$_2$)$_m$O—, —CH$_2$O(CH$_2$)$_s$—, —CH$_2$OCH$_2$C(O)—, —CH$_2$OCH$_2$CH(OH)—, —CH$_2$OCH$_2$C(CH$_3$)$_2$—, —CH$_2$OC(CH$_3$)$_2$CH$_2$—, —C(CH$_3$)$_2$OCH$_2$CH$_2$—, —CH$_2$C(O)OCH$_2$—, —OC(O)CH$_2$CH$_2$—, —C(O)OCH$_2$CH$_2$—, —C(O)OC(CH$_3$)$_2$CH$_2$—, —C(O)OCH$_2$C(CH$_3$)$_2$—, —OCH$_2$(CH$_2$)$_s$—, —OC(CH$_3$)$_2$CH$_2$CH$_2$—, —OCH$_2$C(CH$_3$)$_2$CH$_2$—, —OCH$_2$C(CH$_3$)$_2$—, —OCH$_2$CH=CHCH$_2$—, —OCH$_2$CH(OH)CH$_2$CH$_2$—, —OCH$_2$CH$_2$CH(OH)CH$_2$—, —OCH$_2$C(O)CH$_2$CH$_2$—, —OCH$_2$CH$_2$C(O)CH$_2$—, or a group of the formula

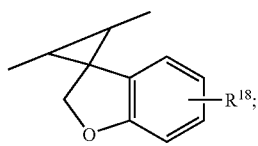

or, where they are attached to adjacent carbon atoms, $R^{13}$ and $R^{14}$ may together represent —OCH$_2$CH$_2$— or —OCH$_2$CH(OH)—, or $R^{13}$ and $R^{14}$ may together form a fused benzene ring;

or, $R^{13}$ and $R^{14}$ together form a C$_{1-2}$alkylene bridge across the pyrrolidine, piperidine or hexamethyleneimine ring to which they are attached;

$R^{15}$ represents hydrogen, $C_{1-6}$alkyl, $(CH_2)_q C_{3-7}$cycloalkyl, $(CH_2)_q$aryl, $(CH_2)_q$heterocyclyl, CHO, $C(O)C_{1-6}$alkyl, $C(O)(CH_2)_q C_{3-7}$cycloalkyl, $C(O)(CH_2)_q$aryl, $C(O)(CH_2)_q$heterocyclyl, $CO_2 C_{1-6}$alkyl, $CO_2(CH_2)_q C_{3-7}$cycloalkyl, $CO_2(CH_2)_q$aryl, $CO_2(CH_2)_q$heterocyclyl or $CO_2(CH_2)_p NR^a R^b$, where $R^a$ and $R^b$ are as previously defined;

or, where they are attached to adjacent carbon atoms, $R^{15}$ and $R^{16}$ may together form a fused imidazolyl or triazolyl ring;

$R^{16}$ and $R^{17}$ each independently represent hydrogen, halogen, hydroxy, $C_{1-6}$alkyl or oxo (=O);

$R^{18}$ represents hydrogen, halogen, hydroxy, $C_{1-4}$alkyl, hydroxy$C_{1-4}$alkyl or fluoro$C_{1-4}$alkyl;

d is 1;

n is zero, 1 or 2;

m is 1 or 2;

p is 1, 2, 3 or 4;

q is zero, 1, 2, 3 or 4; and s is 1, 2 or 3;

or a pharmaceutically acceptable salt or N-oxide thereof.

2. The compound of claim 1 wherein $R^1$ is hydroxy, $C_{1-6}$alkyl, fluoro$C_{1-6}$alkyl, $C_{2-6}$alkenyl, $C_{1-6}$alkoxy, fluoro$C_{1-6}$alkoxy, $C_{2-6}$alkenyloxy, $C_{3-7}$cycloalkoxy, $C_{3-7}$cycloalkyl$C_{1-4}$alkoxy, cyano, NR$^a$R$^b$, SR$^a$, OSO$_2$R$^a$, or $R^1$ together with the group $R^2$ form a 5-membered saturated ring containing one oxygen atom.

3. The compound of claim 1 wherein $R^2$ is hydrogen, fluorine or chlorine.

4. The compound of claim 1 wherein $R^3$ is hydrogen, halogen, fluoro$C_{1-6}$alkyl, fluoro$C_{1-6}$alkoxy, cyano, NR$^a$R$^b$, NR$^a$COR$^d$ (where R$^d$ is methyl, methoxy, trifluoromethyl or phenyl), or a 5-membered aromatic heterocyclic group as defined in claim 1.

5. The compound of claim 1 wherein $R^4$ is hydrogen.

6. The compound of claim 1 wherein $R^5$ is hydrogen, fluorine, chlorine or CF$_3$.

7. The compound of claim 1 wherein $R^6$ is hydrogen.

8. The compound of claim 1 wherein $R^7$ is —(CH$_2$)$_n$NR$^{11}$R$^{12}$ or wherein $R^6$ and $R^7$ together represent =O or —O(CH$_2$)$_m$O— wherein m is 1 or 2.

9. The compound of claim 8 wherein $R^{11}$ represents hydrogen, $C_{1-6}$alkyl, $C_{2-6}$alkenyl, hydroxy$C_{1-6}$alkyl, $(CH_2)_q C_{3-7}$cycloalkyl, $(CH_2)_q$aryl, $(CH_2)_q$heterocyclyl, $C(O)C_{1-6}$alkyl, $C(O)(CH_2)_q$aryl, $C(O)(CH_2)_q$heterocyclyl, $C(O)(CH_2)_p NR^a R^b$, $(CH_2)_q CO_2 C_{1-6}$alkyl, $(CH_2)_p NR^a CO_2 R^b$ or $(CH_2)_q CONR^a$aryl;

and $R^{12}$ represents hydrogen, $C_{1-6}$alkyl, $(CH_2)_q C_{3-7}$cycloalkyl or $CO_2 C_{1-6}$alkyl;

or $R^{11}$ and $R^{12}$ together with the nitrogen atom to which they are attached represent a ring selected from the group consisting of

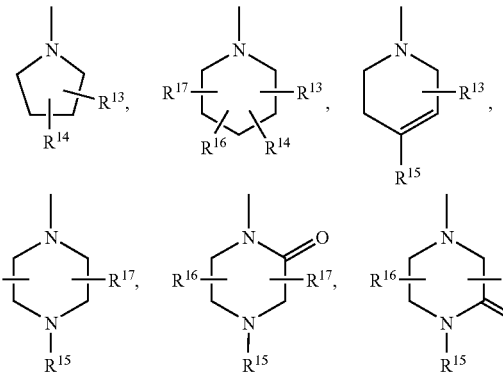

-continued

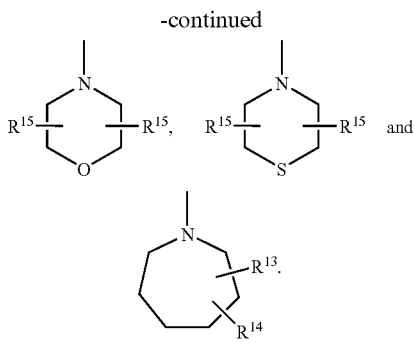

10. The compound of claim 1 wherein $R^8$ is hydrogen, hydroxy, $C_{1-4}$alkyl or $C_{1-4}$alkoxy.

11. The compound of claim 1 wherein $R^9$ and $R^{10}$ each represent hydrogen.

12. The compound of claim 1 of the formula (Ia):

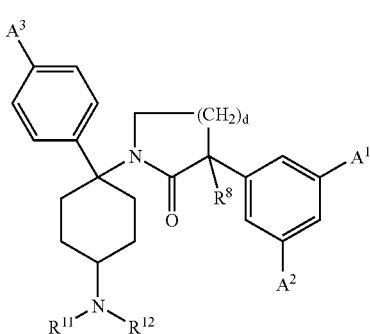

(Ia)

wherein
$A^1$ is fluorine or $CF_3$;
$A^2$ is fluorine or $CF_3$;
$A^3$ is fluorine or hydrogen;
d is 1;
or a pharmaceutically acceptable salt or N-oxide thereof.

13. A compound which is selected from the group consisting of
(RS)-3-[3,5-bis(trifluoromethyl)phenyl]-1-(1,4-dioxa-8-phenylspiro[4.5]decan-8-yl)-2-pyrrolidinone;
(RS)-3-hydroxy-[3,5-bis(trifluoromethyl)phenyl]-1-(1,4-dioxa-8-phenylspiro[4.5]decan-8-yl)-2-pyrrolidinone;
(RS)-3-methyl-[3,5-bis(trifluoromethyl)phenyl]-1-(1,4-dioxa-8-phenylspiro-[4.5]decan-8-yl)-2-pyrrolidinone;
(RS)-3-[3,5-bis(trifluoromethyl)phenyl]-1-(4-oxo-1-phenylcyclohexyl)-2-pyrrolidinone;
(RS)-3-hydroxy-3-[3,5-bis(trifluoromethyl)phenyl]-1-(4-oxo-1-phenylcyclohexyl)-2-pyrrolidinone;
(RS)-3-methyl-3-[3,5-bis(trifluoromethyl)phenyl]-1-(1,4-dioxa-8-phenylspiro[4.5]decan-8-yl)-2-pyrrolidinone;
trans-(RS)-3-[3,5-bis(trifluoromethyl)phenyl]-1-(4-dimethylamino-1-phenylcyclohexyl)-2-pyrrolidinone;
and pharmaceutically acceptable salts and N-oxides thereof.

14. A compound of the formula (I):

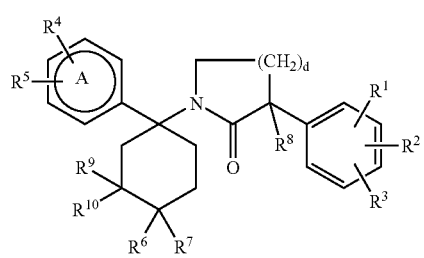

(I)

wherein:
ring A is a phenyl ring;
$R^1$ represents hydroxy, $C_{1-6}$alkyl, fluoro$C_{1-6}$alkyl, $C_{2-6}$alkenyl, $C_{3-7}$cycloalkyl, $C_{3-7}$cycloalkyl$C_{1-4}$alkyl, $C_{1-6}$alkoxy, fluoro$C_{1-6}$alkoxy, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{3-7}$cycloalkoxy, $C_{3-7}$cycloalkyl$C_{1-4}$alkoxy, phenoxy, cyano, halogen, $NR^aR^b$, $SR^a$, $SOR^a$, $SO_2R^a$, $OSO_2R^a$, $NR^aCOR^c$, $COR^a$, $CO_2R^a$ or $CONR^aR^b$ where $R^a$ and $R^b$ each independently represent hydrogen, $C_{1-4}$alkyl, $C_{3-5}$cycloalkyl, fluoro$C_{1-4}$alkyl or $CH_2CO_2C_{1-4}$alkyl, and $R^c$ represents $C_{1-6}$alkyl, $C_{1-6}$alkoxy, fluoro$C_{1-6}$alkyl or phenyl;
$R^2$ represents hydrogen, halogen, $C_{1-6}$alkyl or $C_{1-6}$alkoxy;
or when $R^2$ is adjacent to $R^1$, they may be joined together such that there is formed a 5- or 6-membered saturated or unsaturated ring containing one or two atoms selected from nitrogen, oxygen and sulphur, which ring is optionally substituted by a group selected from $C_{1-4}$alkyl, $CF_3$, =O or =S;
$R^3$ represents hydrogen, halogen, $C_{1-6}$alkyl, fluoro$C_{1-6}$alkyl, $C_{1-6}$alkoxy, fluoro$C_{1-6}$alkoxy, $C_{3-7}$cycloalkyl, $C_{3-7}$cycloalkyl$C_{1-4}$alkyl, cyano, $SR^a$, $SOR^a$, $SO_2R^a$, $NR^aR^b$, $NR^aCOR^c$, $COR^a$, $CO_2R^a$, $CONR^aR^b$ or $C_{1-4}$alkyl substituted by cyano, $CO_2R^a$ or $CONR^aR^b$ where $R^a$, $R^b$ and $R^c$ are as previously defined;
or $R^3$ represents a 5- or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalkyl, $C_{3-7}$cycloalkyl$C_{1-4}$alkyl, trifluoromethyl, $OCF_3$, $NO_2$, $CN$, $SR^a$, $SOR^a$, $SO_2R^a$, $COR^a$, $CO_2R^a$, phenyl, —$(CH_2)_r$—$NR^aR^b$, —$(CH_2)_rNR^aCOR^b$, —$(CH_2)_rCONR^aR^b$, or $CH_2C(O)R^a$, where $R^a$ and $R^b$ are as previously defined and r is zero, 1 or 2;
$R^4$ represents hydrogen, halogen, $C_{1-6}$alkyl, $C_{1-6}$alkoxy, fluoro$C_{1-6}$alkyl, fluoro$C_{1-6}$alkoxy, hydroxy, $NO_2$, $CN$, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;
$R^5$ represents hydrogen, halogen, $C_{1-6}$alkyl, fluoro$C_{1-6}$alkyl or $C_{1-6}$alkoxy substituted by $C_{1-4}$alkoxy;
$R^6$ represents hydrogen, hydroxy or a $C_{1-4}$alkyl group optionally substituted by a hydroxy group;
$R^7$ represents hydrogen, hydroxy, —$(CH_2)_nNR^{11}R_{12}$, —$(CH_2)_nCO_2R^a$, carbocyclyl, C-linked heterocyclyl or heteroaryl, where $R^a$ is as previously defined;
or $R^6$ and $R^7$ together represent =O, =CHCO$_2R^a$ or —$O(CH_2)_mO$—, where $R^a$ is as previously defined;

$R^8$ represents hydrogen, hydroxy, $C_{1-6}$alkyl, $C_{1-6}$alkoxy, hydroxy$C_{1-6}$alkyl, $C_{2-6}$alkenyl, $C_{2-6}$alkynyl, $C_{1-4}$alkyl substituted by $C_{1-4}$alkoxy or $C_{1-6}$alkoxy substituted by $C_{1-4}$alkoxy;

$R^9$ represents hydrogen, halogen or hydroxy and $R^{10}$ represents hydrogen;

or $R^9$ and $R^{10}$ both represent fluorine or together represent oxo (=O);

$R^{11}$ and $R^{12}$ each independently represent hydrogen, $C_{1-6}$alkyl, $C_{2-6}$alkenyl, hydroxy$C_{1-6}$alkyl, $(CH_2)_qC_{3-7}$cycloalkyl, $(CH_2)_q$aryl, $(CH_2)_q$heterocyclyl, CHO, $C(O)C_{1-6}$alkyl, $C(O)(CH_2)_qC_{3-7}$cycloalkyl, $C(O)(CH_2)_q$ aryl, $C(O)(CH_2)_q$heterocyclyl, $C(O)(CH_2)_pNR^aR^b$, $(CH_2)_qCO_2C_{1-6}$alkyl, $CO_2(CH_2)_qC_{3-7}$cycloalkyl, $CO_2(CH_2)_q$aryl, $CO_2(CH_2)_q$heterocyclyl, $CO_2(CH_2)_pNR^aR^b$, $(CH_2)_pNR^aCOR^b$, $(CH_2)_pNR^aCO_2R^b$, $(CH_2)_qCONR^a$aryl or $(CH_2)_qCONR^a$heterocyclyl where $R^a$ and $R^b$ are as previously defined;

or $R^{11}$ and $R^{12}$, together with the nitrogen atom to which they are attached, represent a ring selected from the group consisting of:

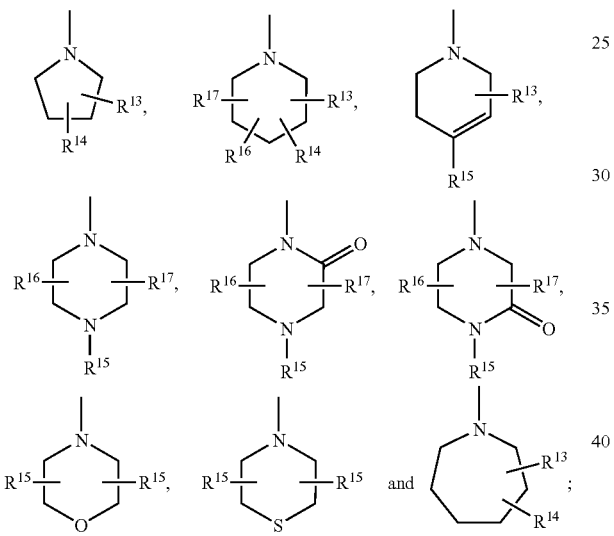

$R^{13}$ and $R^{14}$ each independently represent hydrogen, halogen, hydroxy, $C_{1-6}$alkyl, $C_{2-6}$alkenyl, $C_{2-6}$alkynyl, hydroxy$C_{1-6}$alkyl, fluoro$C_{1-6}$alkyl, $C_{1-6}$alkoxy, $(CH_2)_qC_{3-7}$cycloalkyl, $(CH_2)_q$aryl, $(C_{2-6}$alkenyl)aryl, $(C_{2-6}$alkynyl)aryl, $(CH_2)_q$heterocyclyl, $(CH_2)_qNR^aR^b$, $O(CH_2)_qC_{3-7}$cycloalkyl, $O(CH_2)_q$aryl, $O(CH_2)_q$heterocyclyl, $O(CH_2)_pNR^aR^b$, $OC(O)C_{1-6}$alkyl, $C(O)C_{1-6}$alkyl, $C(O)(CH_2)_q$aryl, $C(O)(CH_2)_q$heterocyclyl, $C(O)(CH_2)_qNR^aR^b$, $CO_2H$, $CO_2C_{1-6}$alkyl, $CO_2(CH_2)_qC_{3-7}$cycloalkyl, $CO_2(CH_2)_q$aryl, $CO_2(CH_2)_q$heterocyclyl or $CO_2(CH_2)_pNR^aR_b$, where $R^a$ and $R^b$ are as previously defined;

or, when they are attached to the same carbon atom, $R^{13}$ and $R^{14}$ may together represent =O, =CHCO$_2R^a$, —O(CH$_2$)$_m$O—, —CH$_2$O(CH$_2$)$_s$—, —CH$_2$OCH$_2$C(O)—, —CH$_2$OCH$_2$CH(OH)—, —CH$_2$OCH$_2$C(CH$_3$)$_2$—, —CH$_2$OC(CH$_3$)$_2$CH$_2$—, —C(CH$_3$)$_2$OCH$_2$CH$_2$—, —CH$_2$C(O)OCH$_2$—, —OC(O)CH$_2$CH$_2$—, —C(O)OCH$_2$CH$_2$—, —C(O)OC(CH$_3$)$_2$CH$_2$—, —C(O)OCH$_2$C(CH$_3$)$_2$—, —OCH$_2$(CH$_2$)$_s$—, —OC(CH$_3$)$_2$CH$_2$CH$_2$—, —OCH$_2$C(CH$_3$)$_2$CH$_2$—, —OCH$_2$C(CH$_3$)$_2$—, —OCH$_2$CH=CHCH$_2$—, —OCH$_2$CH(OH)CH$_2$CH$_2$—, —OCH$_2$CH$_2$CH(OH)CH$_2$—, —OCH$_2$C(O)CH$_2$CH$_2$—, —OCH$_2$CH$_2$C(O)CH$_2$—, or a group of the formula

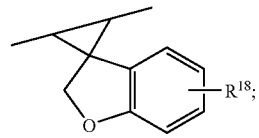

or, where they are attached to adjacent carbon atoms, $R^{13}$ and $R^{14}$ may together represent —OCH$_2$CH$_2$— or —OCH$_2$CH(OH)—, or $R^{13}$ and $R^{14}$ may together form a fused benzene ring;

or, $R^{13}$ and $R^{14}$ together form a $C_{1-2}$alkylene bridge across the pyrrolidine, piperidine or hexamethyleneimine ring to which they are attached;

$R^{15}$ represents hydrogen, $C_{1-6}$alkyl, $(CH_2)_qC_{3-7}$cycloalkyl, $(CH_2)_q$aryl, $(CH_2)_q$heterocyclyl, CHO, C(O)$C_{1-6}$alkyl, $C(O)(CH_2)_qC_{3-7}$cycloalkyl, $C(O)(CH_2)_q$aryl, $C(O)(CH_2)_q$heterocyclyl, $CO_2C_{1-6}$alkyl, $CO_2(CH_2)_qC_{3-7}$cycloalkyl, $CO_2(CH_2)_q$aryl, $CO_2(CH_2)_q$heterocyclyl or $CO_2(CH_2)_pNR^aR^b$, where $R^a$ and $R^b$ are as previously defined;

or, where they are attached to adjacent carbon atoms, $R^{15}$ and $R^{16}$ may together form a fused imidazolyl or triazolyl ring;

$R^{16}$ and $R^{17}$ each independently represent hydrogen, halogen, hydroxy, $C_{1-6}$alkyl or oxo (=O);

$R^{18}$ represents hydrogen, halogen, hydroxy, $C_{1-4}$alkyl, hydroxy$C_{1-4}$alkyl or fluoro$C_{1-4}$alkyl;

d is 1;
n is 1;
m is 1 or 2;
p is 1, 2, 3 or 4;
q is zero, 1, 2, 3 or 4; and
s is 1, 2 or 3;

or a pharmaceutically acceptable salt or N-oxide thereof.

15. A pharmaceutical composition comprising the compound of claim 1 and a pharmaceutically acceptable carrier or excipient.

16. A method for the treatment of pain or inflammation, migraine, emesis, postherpetic neuralgia, depression or anxiety, which method comprises administration to a patient in need thereof of a therapeutically effective amount of the compound of claim 1.

* * * * *